Figure 1A:
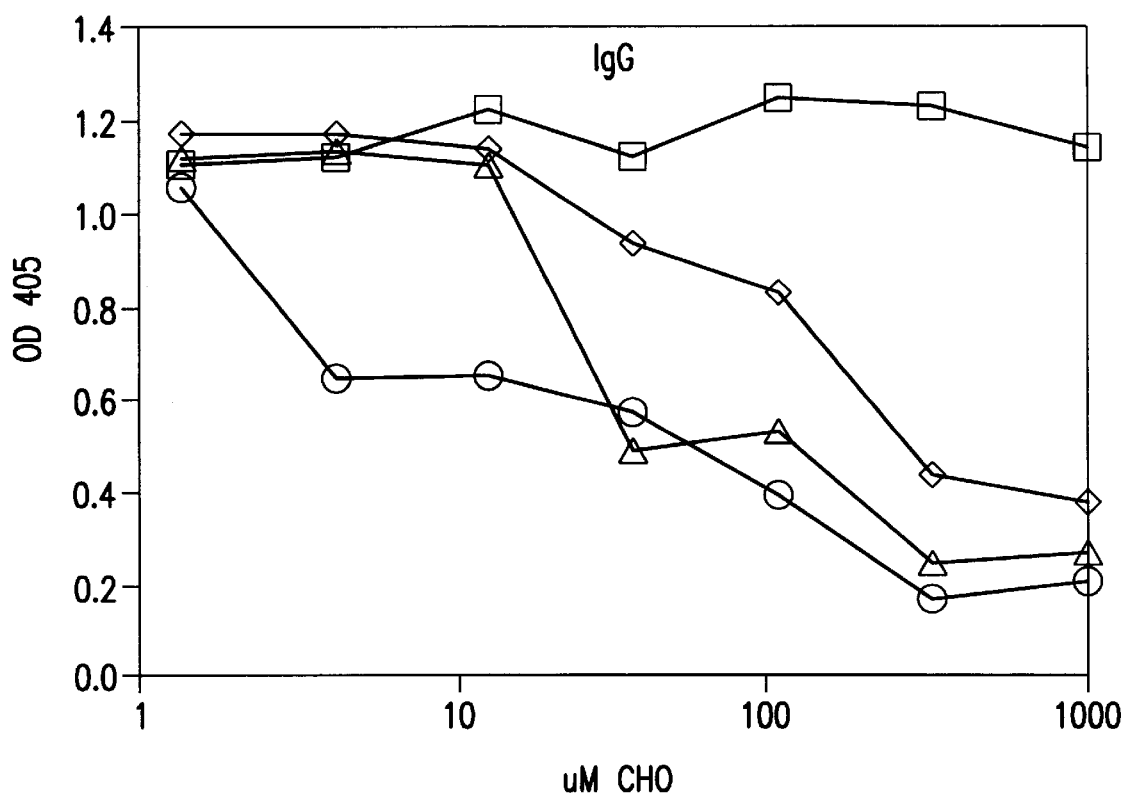

United States Patent [19]
Simon et al.

[11] Patent Number: 6,096,725
[45] Date of Patent: Aug. 1, 2000

[54] METHODS OF USING αGAL OLIGOSACCHARIDES AS IMMUNE SYSTEM TARGETING AGENTS

[75] Inventors: Paul M. Simon, Wilmington, Del.; Edward J. McGuire, Furlong, Pa.

[73] Assignee: Neose Technologies, Inc., Horsham, Pa.

[21] Appl. No.: 08/887,270

[22] Filed: Jul. 2, 1997

[51] Int. Cl.$^7$ ................................................. A61K 31/70
[52] U.S. Cl. ............................... 514/53; 514/54; 514/62; 424/137.1
[58] Field of Search ................................ 514/53, 54, 62; 424/137.1

[56] References Cited

U.S. PATENT DOCUMENTS

| | | | |
|---|---|---|---|
| 5,545,553 | 8/1996 | Gotschlich | 435/252.33 |
| 5,560,911 | 10/1996 | Koren et al. | 424/131.1 |
| 5,651,968 | 7/1997 | Good et al. | 424/140.1 |
| 5,695,759 | 12/1997 | Good et al. | 424/140.1 |
| 5,728,812 | 3/1998 | Koren et al. | 530/387.2 |
| 5,767,093 | 6/1998 | Good et al. | 514/25 |
| 5,874,261 | 2/1999 | Roth | 435/97 |

FOREIGN PATENT DOCUMENTS

| | | |
|---|---|---|
| 0 510 949 B1 | 1/1997 | European Pat. Off. . |
| 0 510 949 A2 | 10/1997 | European Pat. Off. . |
| WO 93/03735 | 3/1993 | WIPO . |
| WO 93/13198 | 7/1993 | WIPO . |
| WO 94/03184 | 2/1994 | WIPO . |

OTHER PUBLICATIONS

Taniguchi et al., 1996, "In vivo immunoadsorption of antipig antibodies in baboons using a specific GALα1–3GAL col.", *Transplantation* 62:1379–1384.

Lussow et al., 1996, "Targeting Of Antihapten Antibodies To Activated T Cells Via An IL–2–Hapten Conjugate Prolongs Cardiac Graft Survival", *Transplantation* 62:1703–1708.

Lussow et al., 1996, "Redirecting Circulating Antibodies via Ligand–Hapten Conjugates Eliminates Target Cells In Vivo", *Journal of Immunotherapy* 19:257–265.

1991, Mtg. Rpt. of the Second Intl. Conf. on Biospecific Antibodies and Targeted Cellular Toxicity, *Immunol. Today* 12:51–54.

Alexandre et al., 1987, "Present experiences in a series of 26 ABO–incompatible living donor renal allografts", *Transplant Proc.* 19:4538–4542.

Arumugham et al., 1986, "Structures of the asparagine–linked sugar chains of laminin", *Biochim. Biophys. Acta* 883:112–126.

H. Auchincloss, 1988, "Xenogeneic transplantation", *Transplantation* 46:1–20.

Bach et al., 1991, "Accommodation: A working paradigm for progressing toward clinical discordant xenografting", *Transpl. Proc.* 23:205–207.

Bannett et al., 1987, "Experiences with known ABO–mismatched renal transplants", *Transplant Proc.* 19:4543–4546.

Bouwman et al., 1989, "Prolongation of graft survival in hamster to rat xenografting", *Transplant Proc.* 21:540–541.

Bouwman et al., 1989, "Prolongation of graft survival in sensitized xenotransplantation", *Transplant Proc.* 21:551–552.

Brodsky et al., 1982, "Evolution of HLA antigenic determinants: Species cross–reactions of monoclonal antibodies", *Immunogenetics* 15:151–166.

Cameron et al., 1983, "Characterization of the preformed involved in the xenograft reaction", *J. Surg. Oncol.* 22:157–163.

Chavez–Peon et al., 1971, "Humoral factors in experimental renal allograft and xenograft rejection", *Transplant Proc.* 3:573–576.

Choe et al., 1996, "The β–chemokine receptors CCR3 and CCR5 facilitates by primary HIV–1 isolates", *Cell* 85:1135–1148.

Collins et al., 1994, "Characterization of porcine endothelial cell determinants recognized by human natural antibodies", *Xenotransplantation* 1:36–46.

Collins et al., 1995, "Cardiac xenografts between primate species provide for the importance of the α–galactosyl determinant in hyperacute rejection[1]", *J. Immunol.* 154:5500–5510.

Connor et al., 1994, Receptor specificity in human, avian, and equine H2 and H3 influenza virus isolates, *Virology* 205:17–23.

Cooper et al., 1988, "Effects of cyclosporine and antibody adsorption on pig cardiac xenograft survival in the baboon", *J. Heart Transplant* 7:238–246.

D. Cooper, 1990, "Immediate postoperative care and maintenance immunosuppressive therapy", *The Transplantation and Replacement of Throacic Organs*, Cooper & Novitzky (eds.), Kluwer Academic Publishers, pp. 89–99.

Cooper et al., 1991, "The pig as potential organ donor for man", *Xenotransplantation: The Transplantation of Organs and Tissues Between Species* pp. 481–500.

Cooper et al., 1993, "Specific intravenous carbohydrate therapy", *Transplantation* 56:769–777.

Cozzi et al., "Expression of human decay accelerating factor in transgenic pigs", *Transplant. Proc.* 26:1402–1403. (Second Intl Congress on Xenotransplantation Abstr 57.).

Dalmasso et al., 1992, "Mechanism of complement activation in the hyperacute rejection of porcine organs transplanted into primate recipients", *Am. J. Pathol.* 140:1157–1166.

(List continued on next page.)

*Primary Examiner*—Howard C. Lee
*Attorney, Agent, or Firm*—Pennie & Edmonds LLP

[57] ABSTRACT

The invention relates to methods for attenuating xenograft rejection in humans and old world monkeys, using oligosaccharides containing a Galα1-3Gal motif, to neutralize or remove anti-αGal antibodies. The invention additionally relates to methods for site directed activation of the complement cascade or host leukocytes using oligosaccharides containing a Galα1-3Gal motif to target anti-αGal antibodies. The invention further relates to pharmaceutical compositions that may be used in the practice of the invention. Such compositions contain, as the active ingredient, an oligosaccharide containing a Galα1-3Gal motif effective in binding anti-αGal antibodies in vivo or ex vivo.

8 Claims, 11 Drawing Sheets

OTHER PUBLICATIONS

Dalmasso et al., 1992, "The complement system in xenotransplanatation", *Immunopharmacology* 24:149–160.

Dieffenbach & Dvesksler, 1995, *PCR Primer, A Laboratory Manual*, Cold Spring Harbor Laboratory Press, New York. (Index only).

Donohue et al., 1990, "Enhanced in vitro lysis of human ovarian carcinomas with activated peripheral blood lymphocytes and bifunctional immune heteroaggregates[1]", *Cancer Res.* 50:6508–6514.

Feng et al., 1996, "HIV–1 entry cofactor: Functional cDNA cloning of a seven–transmembrance, G protein–coupled receptor", *Science* 272:872–876.

Fischel et al., 1992, "Cardiac xenografting in the pig–to–rhesus monkey model: Manipulation of antiendothelial antibody prolongs survival", *J. Heart Lung Transplant* 11:965–974.

Forty et al., 1993, "Activation of the alternative pathway of complement in hyperacute xenograft rejection of rabbit hearts by human blood", *J. Heart Lung Transpl.* 12:283–287.

Galili et al., 1988, "Interaction between human natural anti–α–galactosyl immunoglobulin G and bacteria of the human flora", *Infect. & Immun.* 56:1730–1737.

Galili et al., 1993, "Interaction of the natural anti–Gal antibody with α–galactosyl epitopes: A major obstacle for xenotransplantation in humans", *Immunol. Today* 14:480–482.

Gambiez et al., 1992, "The role of natural lgM in the hyperacute rejection of discordant heart xenografts", *Transplantation* 54:577–583.

Garrido et al., 1990, "Targeting human T–lymphocytes with bispecific antibodies to react against human ovarian carcinoma cells growing in nu/nu mice", *Cancer Res.* 50:4227–4232.

Garver et al., 1980, "Evidence of similar organization of the chromosomes carrying the major histocompatibility complex in man and other primates", *Cytogenetics & Cell Genetics* 27:238–245.

Geller et al., 1993, "Evidence that polyreactive antibodies are deposited in rejected discordant xenografts", *Transplantation* 55:168–172.

Giles et al., 1970, "Mechanism and modification of rejcetion of heterografts between divergent species", *Transplant Proc.* 2:522–537.

Goldberg et a, 1995, "Inhibition of the human antipig xenograft reaction with soluble oligosaccharides", *Transplant Proc.* 27:249–250.

Good et al., 1992, "Identification of carbohydrate structures that bind human antiporcine antibodies: Implications for disordant xenografting in humans", *Transplant Proc.* 24:559–562.

C. Hammer, 1989, "Preformed natural antibodies (PNAB) and possibilities of modulation of hyperacute xenogeneic rejection (HXAR)", *Transplant. Proc.* 21:522–523.

C. Hammer, 1989, "Evolutionary considerations in xenotransplantation", *Xenograft* 25:115–123.

Hammer et al., 1991, "Evolutionary, physiological, and immunological considerations in defining a suitable donor for man", *Xenotransplantation: The Transplantation of Organs and Tissues Between Species* pp. 429–438.

Holgersson et al., 1990, "Structural characterization of non–acid glycosphingolipids in kidneys of single blood group O and A pigs", *J. Biochem.* 108:766–777.

Holgersson et al., 1991, "Carbohydrate antigen specificity of pig lymphocytotoxic IGM antibodies produced by two EBV transformed human B cell lines", *Glyconj. J.* 8:172.

Holzknecht & Platt, 1995, "Identification of porcine endothelial cell membrane antigens recognized by human xenoreactive natural antibodies", *J. Immunol.* 154:4565–4575.

Ildstad et al., 1992, "Mixed xenogeneic chimeras (rat + mouse to mouse); evidence of rat stem cell engraftment, strain–specific transplantation tolerence, and skin–specific antigens", *Transplantation* 53:815–822.

Ildstad et al., 1992, "Cross–species transplantation tolerance: Rat bone marrow–derived cells can contribute to the ligand for negative selection of mouse T cell receptor Vβ in chimeras tolerant to xenogeneic antigens (mouse + rat→mouse)", *J. Exp. Med.* 175:147–155.

Inverardi & Pardi, 1994, "Early events in cell–mediated recognition of vascularized xenografts: Cooperative interactions between selected lymphocyte subsets and natural antibodies", *Immunol. Rev.* 141:71–93.

Johnston et al., 1992, "Discordant xenograft rejection in an antibody–free model", *Transplantation* 54:573–576.

Kaplon et al., 1995, "Absence of hyperacute rejection in newborn pig–to–baboon cardiac xenografts", *Transplantation* 59:1–6.

Langford et al., 1993, "Production of pigs transgenic for human decay accelerating factor", *Transplant. Proc.* 26:1400–1401. (Second Intl Congress on Xenotransplantation Abstr. 56.)

Lexer et al., 1986, "Hyperacute rejection in a discordant (pig to baboon) cardiac xenograft model", *J. Heart Transplant* 5:411–418.

Lesnikoski et al., 1995, "Endothelial and host mononuclear cell activation and cytokine expression during rejection of pig–to–baboon discordant xenografts", Transplant. Proc. 27:290–291. (Abstracts of the 15th World Congress of the Transplantation Soc. Transplantation Proceedings.).

Lloyd et al., 1968, "Immunochemical studies on blood groups, XXXVIII, structures and activities of oligosaccharides produced by alkaline degradation of blood–group Lewis$^a$ substance. Proposed structure of the carbohydrate chains of human blood–group A, B,H, Le$^a$, and Le$^b$ substances*", *Biochem.* 7:2976–2990.

Lu et al., 1994, "Xenotransplantation", *FASEF J.* 8:1122–1130.

Lussow et al., 1996, "Targeting of activated T–cells with natural cytotoxic antibodies via an IL2–hapten conjugate prolongs graft survival", *Transplantation Proc.* 28:571–572.

Michler, 1987,"Prolongation of primate cardiac xenograft survival with cyclosporine", *Transplantation* 44:632–636.

Miyagawa et al., 1988, "The mechanism of discordant xenograft rejection", *Transplantation* 46:825–830.

Monden et al., 1989, "A crucial effect of splenectomy on prolonging cardiac xenograft survival in combination with cyclosporine", *Surgery* 105:535–542.

Neethling et al., 1994, "Protection of pig kidney (PK15) cells from the cytotoxic effect of anti–pig antibodies by α–galactosyl oligosaccharides", *Transplantation* 57:959–963.

Neethling et al., 1996, "The reducing end of αgal oligosaccharides contributes to their efficiency in blocking natural antibodies of human and baboon sera", *Transplantation Intl.* 9:98–101.

Neubauer et al., 1981, "Reactivity of monoclonal antibodies against human leucocyte antigens with lymphocytes of non–human primate origin", *J. Immunogenetics* 8:433–442.

Parker et al., 1994, "Characterization and affinity isolation of xenoreactive human natural antibodies", *J. Immunol.* 153:3791–3803.

Parker et al., 1995, "Xenoreactive natural antibodies in the world of natural antibodies: Typical or unique?", *Transpl. Immunol.* 3:181–191.

Perper & Najarian, 1966, "Experimental renal heterotransplantation", *Transplantation* 4:337–388.

Perper et al., 1967, "Experimental renal heterotransplantation III. Passive transfer of transplantation", *Transplantation* 5:514–533.

Platt et al., 1990, "An ELISA assay for xenoreactive natural antibodies", *Transplantation* 49:1000–1001.

Platt et al., 1990, "Endothelial cell antigens recongnized by xenoreactive human natural antibodies", *Transplantation* 50:817–822.

Platt et al., 1990, "Transplantation of discordant xenografts: A review of progress", *Immunol. Today* 11:450–457.

Platt et al., 1991, "Immunopathology of hyperacute xenograft rejection in a swine–to–primate model", *Transplantation* 52:214–220.

J. Platt, 1994, "A perspective on xenograft rejection and accommodation", *Immunol. Rev.* 141:127–149.

Ricordi et al., 1992, "Islet xenografts in fully xenogeneic (rat→mouse) chimeras: Evidence for normal regulation of function in a xenogeneic mouse environment", *Surgery* 112:327–332.

Ryu et al., 1994, "Structures of an HIV and MHC binding fragment from human CD4 as refined in two crystal lattices", *Structure* 2:59–74.

Sachs et al., 1971, "The immunologic response to xenografts: Recognition of mouse H–2 histocompatibility antigens by the rat", *J. Immunol.* 107:481–492.

Sakihama et al., 1995, "Oligomerization of CD4 is required for stable binding to class II major histocompatibility complex proteins but not for interaction with human immunodeficiency virus gp120", *Proc. Natl. Acad. Sci. USA* 92:6444–6448.

Samson et al., 1996, "Molecular cloning and functional expression of a new human CC–chemokine receptor gene", *Biochemistry* 35:3362–3367.

Samuelsson et al., 1994, "Natural antibodies and human xenotransplantation", *Immunol. Rev.* 141:151–168.

Sandrin et al., 1995, "Enzymatic remodelling of the carbohydrates surface of a xenogenic cell substantially reduces human antibody binding and complement–mediated cytolysis", *Nature Med.* 1:1261–1267.

Sandrin et al., 1996, "Reduction of the major porcine xenoantigen gal$\alpha$(1,3)gal by expression of $\alpha$(1,2)fucosyltransferase", *Xenotranspl.* 3:134–140.

Segal et al., 1989, "Targeting of cytotoxic cells against tumors with heterocrosslinked, bispecific antibodies", *Princess Takamatsu Symp.* 19:323–331.

Simpson & Monaco, 1989, "Immunosuppression in xenotransplantation", *Xenograft* 25:273–284.

Stanton et al., (eds.), 1986, *Swine in Cardiovascular Research* CRC Press, FL., vol. 1 & 2, Chapter 1, pp. 1–3.

Stark, et al., 1991, "Immunological compatibility between the chacma baboon and man", *Transplantation* 52:1072–1078.

Starzl et al., 1993, "Baboon–to–human liver transplantation", *Lancet* 341:65–71.

Y. Suzuki, 1994, "Gangliosides as influenza virus receptors. Variation of influenza viruses and their recognition of the receptor sialo–sugar chains", *Prog. Lip. Res.* 33:429–457.

Tanaka et al., 1994, "Xenotransplantation from pig to cynomolgus monkey: The potential for overcoming xenograft rejection through induction of chimerism", *Transplant. Proc.* 26:1326–1327. (Second Intl Congress on Xenotransplantation Abstr. 122.)

M.E. Tumbleson (ed.), 1985, *Swine in Biomedical Research*, vol. 3 (Index only).

Tuso et al., 1993, "Pig aortic endothelial cell antigens recogized by human IgM natural antibodies", *Transplantation* 56:651–655.

Tuso et al., 1993, "Characterization of human antibodies that are cytotoxic to pig aortic endothelial cells", *Transplant Proc.* 25:392–393.

Valdivia et al., 1990, "Evidence that deoxyspergualin prevents sensitization and first–set cardiac xenograft rejection in rats by suppression of antibody formation", *Transplantation* 50:132–136.

van Dijk et al., 1989, "Bispecific antibodies reactive with the multidrug–resistance–related glycoprotein and CD3 induce lysis of multidrug–resistant tumor cells", *Int. J. Cancer* 44:738–743.

Wang et al., 1992, "Immunofluorescent localization of pig complement component 3, regardless of the presence or absence of detectable immunoglobulins, in hyperacutely rejected heart xenografts", *Histochem.* 24:102–109.

W.M. Watkins, 1974, "Genetic regulation of the structure of blood–group–specific glycoproteins", *Biochem. Soc. Symp.* 40:125–146.

W.M. Watkins, 1980, "Biochemistry and genetics of the ABO, Lewis and P blood group systems", *Advances in Human Genetics* Harris & Hirschhorn (eds.), Plenum, NY 10:1–136.

Ye & Cooper, 1991, "Experimental xenotransplantation in nonhuman primates using distantly related donor species", *Xenotransplantation* pp. 389–393.

Ye et al., 1994, "Evidence that intravenously administered $\alpha$–galactosyl carbohydrates reduce baboon serum cytotoxicity to pig kidney cells (PK15) and transplanted pig hearts", *Transplantation* 58:330–337.

Zeng et al., 1992, "Long–term survival of donor–specific pancreatic islet xenografts in fully xenogeneic chimeras (F344 rat to B10 mouse)", *Transpl. Proc.* 24:641.

Zeng et al., 1992, "Long–term survival of donor–specific pancreatic islet xenografts in fully xenogeneic chimeras (WF rat to B10 mouse)", *Transpl. Proc.* 53:277–283.

Zhao et al., 1994, "Hyperacute xenograft rejection in the swine–to–human donor–recipient combination", *Transplantation* 57:245–249.

Zopf & Roth, 1996, "Oligosaccharide anti–infective agents", *The Lancet* 347:1017–1021.

Galili et al., "Inhibition of Anti–Gal lgG Binding to Procine Endothelial Cells by Synthetic Oligosaccharides", Transplantation, vol. 62(2): 256–262, Jul. 27, 1996.

Cairns et al., "Inhibition of thePig to Human Xenograft Reaction, Using Soluble Gal-alpha1–3Gal and Gal-alpha1–3Gal-beta1–4GIcNAc", Transplantation, vol. 60(11): 1202–1207, Dec. 1995.

Cooper et al., "Manipulation of the anti–alphaGal antibody–alphaGal epitope system in experimental discordant xenotransplantation", Xenotransplantation, vol. 3:102–111, 1996.

Cooper et al., "Oligosaccharides and Discordant Xenotransplantation", Immunological Reviews, No. 141: 31–58, 1994.

Nagasaka et al., "alpha–Galctosyl Oligosaccharides Conjugated with Polyethylene Glycol as Potential Inhibitors of Hyperacute Rejection upon Xenotransplantation", Biochem., Biophys. Res. Commun., vol. 232: 731–736, 1997.

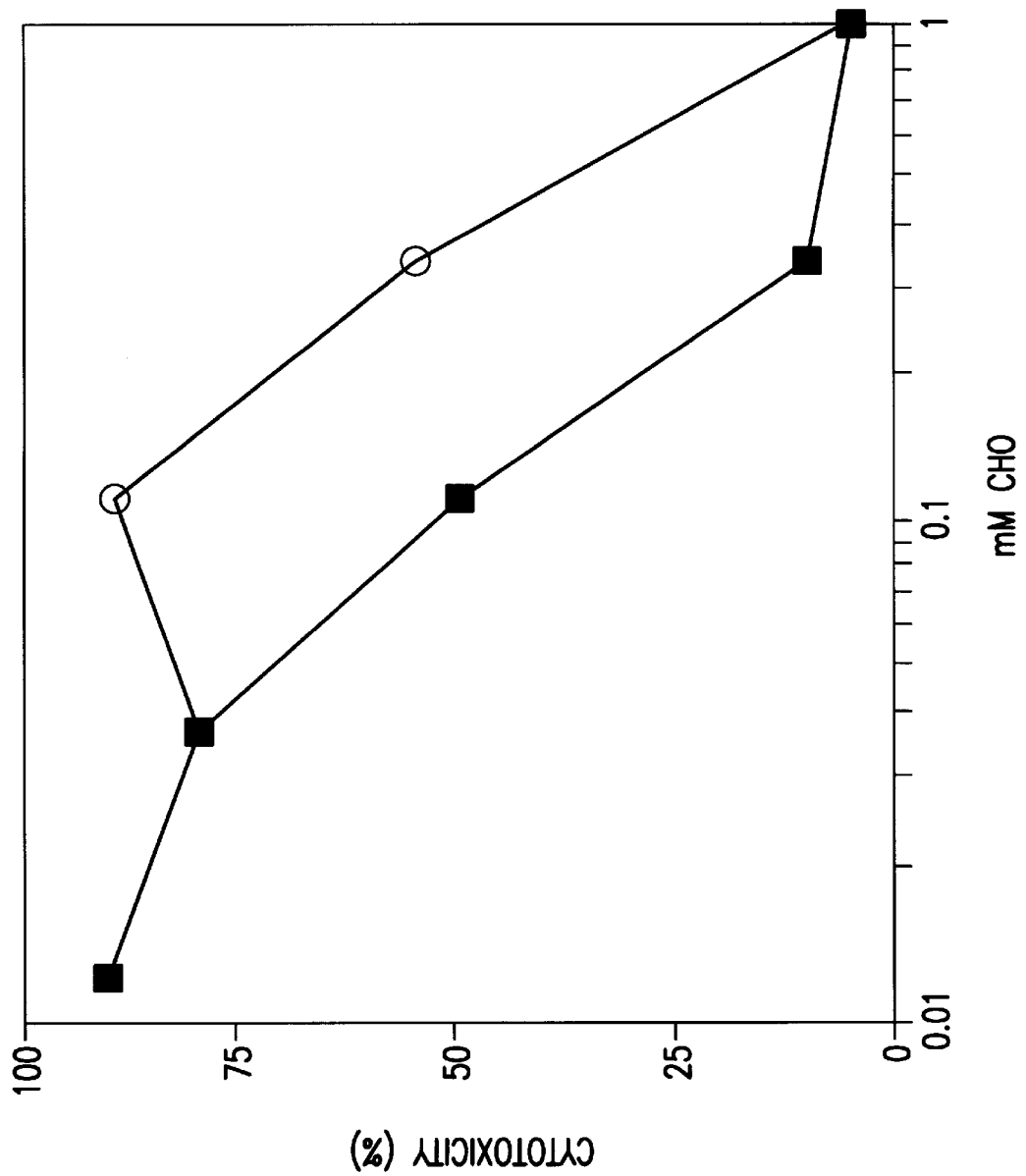

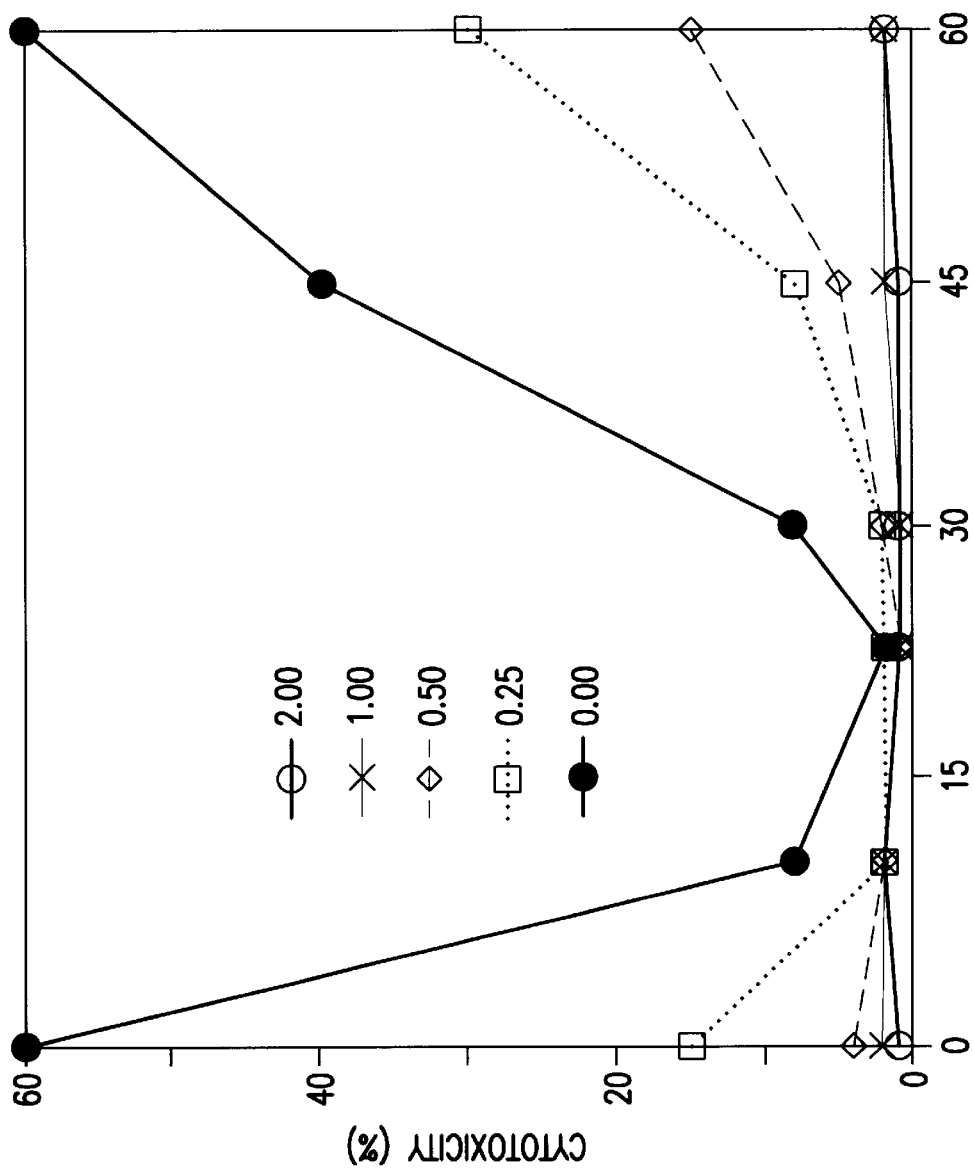

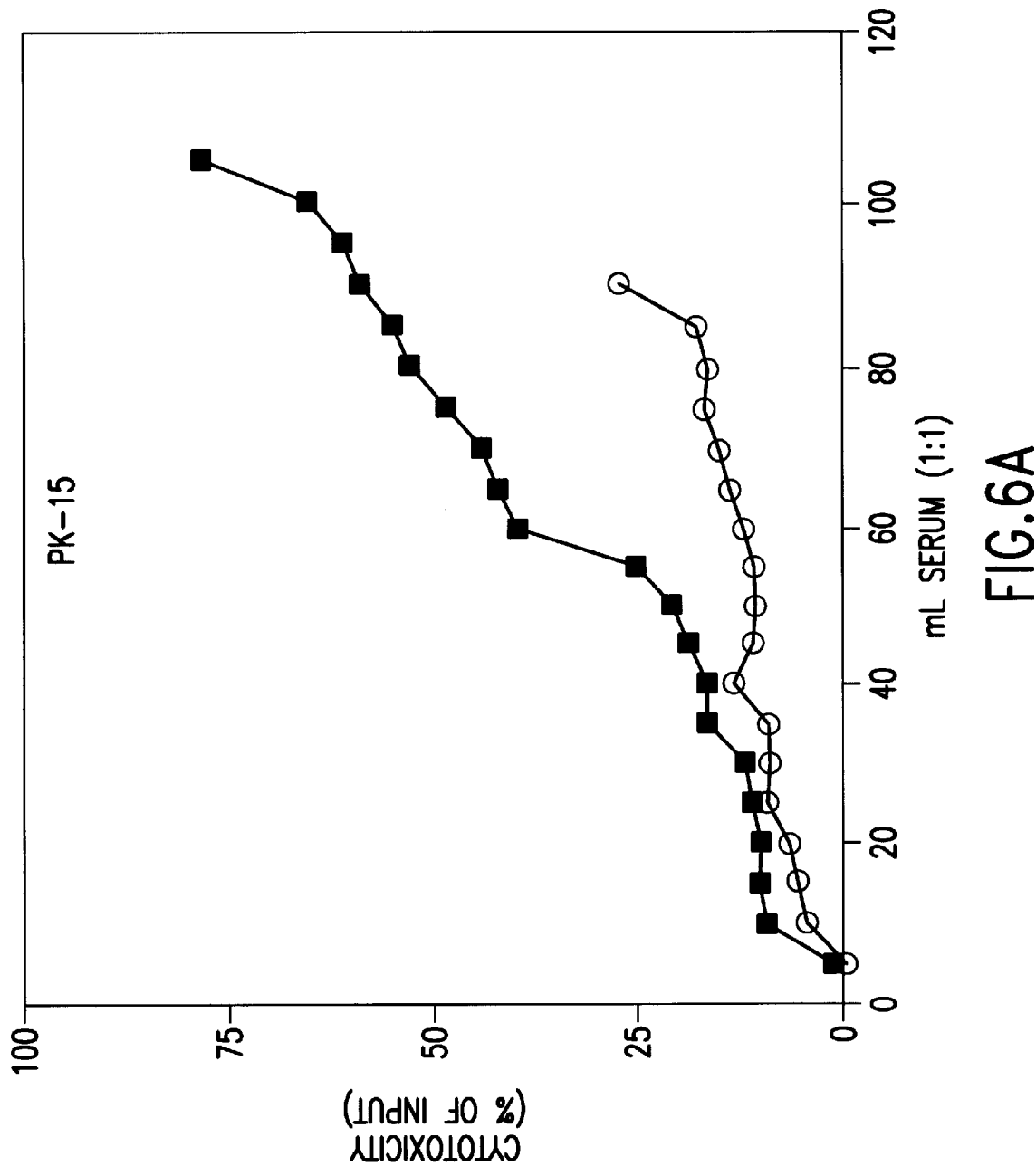

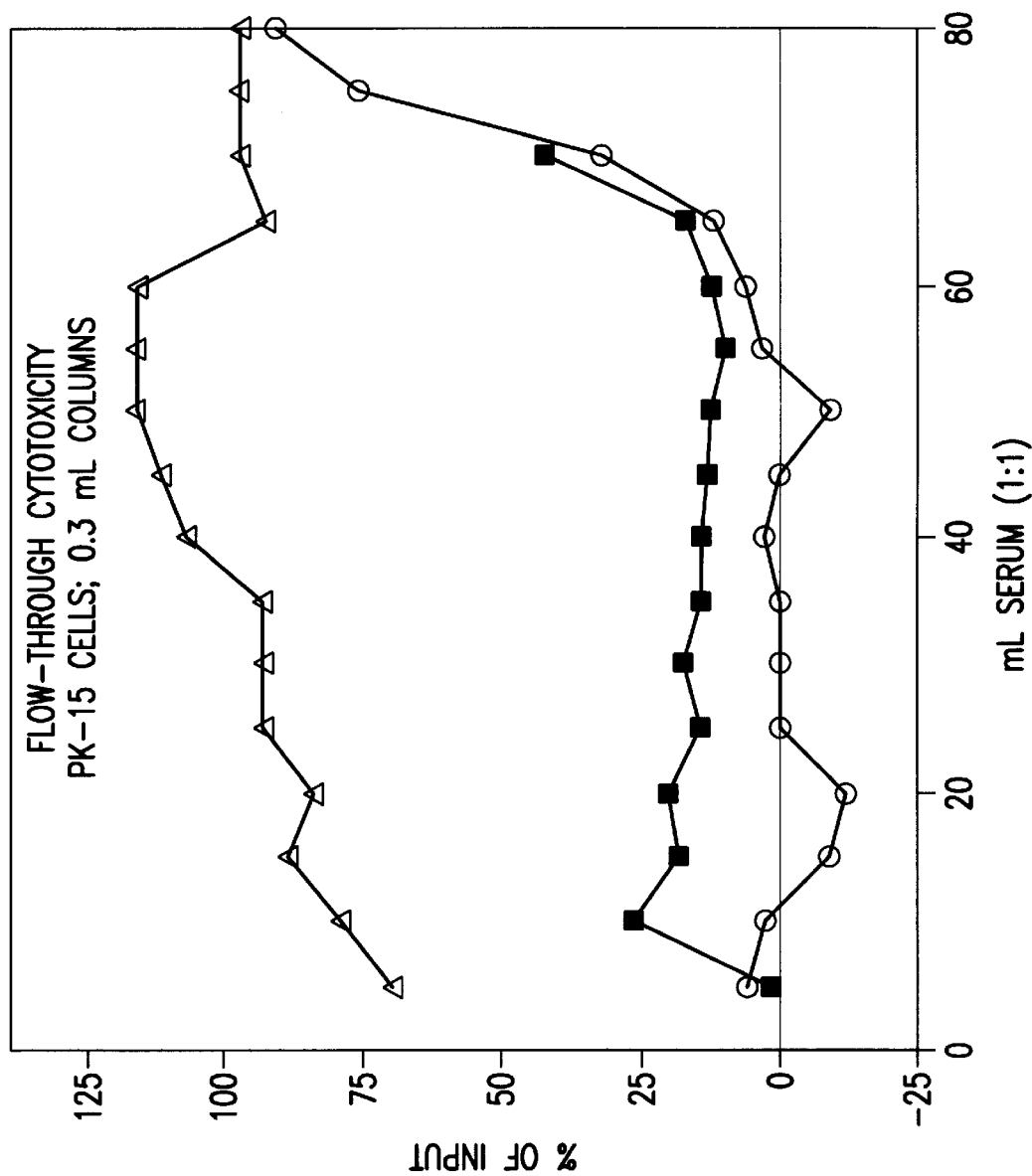

METHODS OF USING αGAL OLIGOSACCHARIDES AS IMMUNE SYSTEM TARGETING AGENTS

1. INTRODUCTION

The invention relates to methods for attenuating xenograft rejection in humans and old world monkeys, using oligosaccharides containing a Galα1-3Gal motif, to neutralize or remove anti-αGal antibodies. The invention additionally relates to methods for site directed activation of the complement cascade using oligosaccharides containing a Galα1-3Gal motif to target anti-αGal antibodies. The invention further relates to pharmaceutical compositions that may be used in the practice of the invention. Such compositions contain, as the active ingredient, an oligosaccharide containing a Galα1-3Gal motif effective in binding anti-αGal antibodies in vivo or ex vivo.

2. BACKGROUND OF THE INVENTION

2.1. XENOGRAFT REJECTION

Advances in organ transplantation surgery and the development of effective immunosuppressive drug regimens has made organ transplantation a nearly routine procedure. The shortage of human donor organs is the principal obstacle in the transplantation field. Only a fraction of transplantation candidates receive grafts, and many patients are not even listed as candidates owing to this shortage. In addition, a number of diseases (e.g., diabetes) do not include transplantation as a viable option at this time. However, this perspective could change if transplantation options were more permissive. Accordingly, much attention has recently been placed on alternative animal organ donor sources. Higher primates are immunologically most suitable and have been used as organ donors in a few cases, but are difficult and uneconomical to breed, may impose a high risk of viral transmission and their widescale use in clinical transplantation is likely to raise ethical objections. Consequently, focus has been placed upon use of the pig as an organ donor. Swine constitute an attractive source of organ donors for clinical transplantation because they are plentiful, can be easily bred in captivity, have anatomical and physiologic compatibility with humans and are amenable to genetic manipulation (Cooper et al., 1991, in Xenotransplantation: the transplantation of organs and tissues between species, 481–500 (Springer, Berlin); Tumbleson, M. E. (ed.) 1985, Swine in biomedical Research, Volume 3 (Plenum, N.Y.); Stanton et al. (eds.), 1986 Swine in Cardiovascular Research, Vol. I–III (CRC Press, Florida)).

Transplantation between individuals of the same species or between closely related species is called concordant, and between more distant species, discordant. The management of concordant graft rejection is now possible with immunosuppressive therapy. In contrast, discordant transplantation, such as that between pig and human or old world monkey, is characterized by hyperacute rejection ("HAR"), an extremely rapid immunological attack by preformed host antibodies which recognize molecular structures expressed on the endothelial cell surface of vascularized grafts (Starzl et al., 1993, Lancet 341:65; Auchincloss, H. 1988, Transplantation 46:1; Tuso et al., 1993, Transplantation 56:651; Inverardi et al., 1994, Immunol Rev. 141:71–93). Vascularized grafts performed between discordant species undergo hyperacute rejection within minutes of implant and can lead to graft destruction within approximately 5–20 minutes in the case of a swine to old world monkey transplantation. The mechanisms that mediate hyperacute rejection are not susceptible to conventional immunosuppressive therapy (Auchincloss, H. 1988, Transplantation 46:1). Recent studies have suggested that if HAR is weathered by the transplanted organ, the transplanted organ "accommodates" to the host, and its long-term survival becomes manageable by more conventional immunosuppressive drugs (Platt, J., 1994, Immunol. Rev. 141:127–149; Bach et al., 1991, Transpl. Proc. 23(1):205–207). There is therefore a great need for developing innovative methods and compositions capable of achieving clinically significant prolongation of xenograft function and survival by overcoming hyperacute rejection (Platt et al., 1990, Immunol. Today 11:450).

In swine to old world monkey combinations, the recognition and binding of antigens expressed on the endothelium of the donor organ by preformed xenoreactive IgM antibodies of recipient origin is considered the major immediate mediator of graft endothelial cell injury through complement-dependent hyperacute rejection (Platt et al., 1991, Transplantation 52:214; Dalmasso et al, 1992, Immunopharmacology 24:149). This role of xenoreactive antibodies in the immediate recognition of a xenogeneic organ is suggested by observations that: perfusion of xenogeneic organs results in the selective depletion of xenoreactive natural antibodies from the blood (Perper et al., 1966, Transplantation 4:337–388; Platt et al., 1990, Transplantation 49:1000–1001; Giles et al., 1970, Transplant Proc. 2:522–537; Cooper et al., 1988, J. Heart Transplant 7:238–246; Fischel et al., 1992, J. Heart Lung Transplant 11:965–974; Holzknecht et al., 1995, J. Immunol. 154:4565–4575), depletion of xenoreactive antibodies through perfusion of xenogeneic organs delays hyperacute rejection of a xenograft even when the complement system remains intact (Dalmasso et al., 1992, Am. J. Pathol. 140:1157–1166), hyperacute rejection does not occur when swine hearts are transplanted into newborn old world monkeys which have an intact complement system but very low levels of natural antibodies (Kaplan et al., 1994, Transplantation 59:1–6), infusion of antidonor antibodies may initiate the rejection of a xenogeneic organ graft (Perper et al., 1967, Transplantation 5:514–533; Chavez-Peon et al., 1971, Transplant Proc. 3:573–576) and specific inhibition of the binding of natural antibodies delays the onset of hyperacute rejection (Gamblez et al., 1992, Transplantation 54:577–583; Ye et al., 1994 Transplantation 58:330–337).

The histo-blood group A and B epitopes, against which anti-A and anti-B antibodies are directed, are structurally defined trisaccharides (Lloyd et al., 1968, Biochemistry 7:2976; Watkins, W. M., 1974, Biochem. Soc. Symp. 40:125; Watkins, W. M., 1980, Biochemistry and genetics of the ABO, Lewis and P blood group systems, In: Advances in Human Genetics, Harris and Hirschhorn (eds), Vol. 10, Plenum, New York, p. 1). Baboons "hyperimmunized" to the incompatible donor group through intravenous injection of a composition containing the incompatible donor trisaccharide reject heterotopic allografted ABO-incompatible donor hearts through hyperacute antibody-mediated vascular rejection within a mean of 19 minutes. Continuous intravenous infusion of the incompatible A or B donor group trisaccharide and/or ex vivo depletion with this immobilized trisaccharide, beginning immediately pre-transplantation and continued post-transplantation for several days, has been observed to prolong allograft survival to a mean of 8 days (Cooper et al., 1993, Transplantation, 56:769–777). While these results have led to speculation that the ABO system serves as a model for HAR of xenografts, unlike the group A and B epitopes, the epitope(s) bound by anti-animal antibodies that are determinative of xenograft rejection, have not been structurally characterized thoroughly and effective anti-animal antibody blocking substances have not been described.

Xenoreactive natural antibodies have been shown to play a major role in initiating HAR in the case of old world monkey rejection of a swine xenograft, since their depletion appears to prevent complement activation and abrogates HAR, potentially allowing prolongation of xenograft survival for variable periods (Lu et al., 1994, FASEB, J. 8:1122–1130; Platt et al., 1990, Transplantation 50:817–822). On the other hand, rejection of vascularized discordant xenogeneic organs inevitably takes place after these treatments, suggesting that other mechanisms must be involved in the recognition of the grafts. For example, an induced antibody response may take place, due to sensitization of the recipient (Valvidia et al., 1990, Transplantation 50:132; Monden et al., 1989, Surgery 105:535; Bouwman et al., 1989, Transplant Proc. 21:551; Bouwman et al., Transplant Proc. 21:540; Sachs et al., 1971, J. Immunol. 107:481). Additionally, the alternative pathway for complement activation, which can act in the absence of antibodies, has also been implicated in xenograft rejection and may be capable of at least partially substituting for the direct antibody-dependent pathway (Zhao et al., 1994, Transplantation 57:245; Forty et al., 1993, J. Heart Lung Transpl. 12:283; Wang et al., 1992, Histochem. T. 24:102; Miygawa et al., 1988, Transplantation 46:825; Johnston et al., 1992, Transplantation 54:573). These data suggest that since complement deposition could be observed in a transplanted xenogeneic organ in the absence of Ig deposition, mechanisms leading to rejection may be triggered even if natural xenoreactive antibodies are neutralized or removed from recipient serum.

2.2. αGAL EPITOPE

In recent years, much attention has been focused on defining the molecular structures that are recognized by xenophilic natural antibodies, leading to activation of the complement cascade and eventually, to hyperacute rejection. Most evidence now points to the oligosaccharide epitope Galα1-3Gal ("αGal") as the major target of xenoreactive natural antibodies. Humans and old world monkeys do not express the αGal epitope because they lack a functional gene encoding the enzyme α1-3galactosyl transferase that forms the unfucosylated "linear B" epitope Galα1-3Galβ1-4GlcNAc, which in other mammalian cells causes terminal glycosylation of many glycoproteins, including those expressed by endothelial cells, leukocytes and red blood cells (Galili, et al., 1993, Immunol. Today 14:480–482). Initial evidence of the importance of the αGal epitope was provided by studies in which antibodies from porcine organs perfused by human plasma were eluted and tested for binding to immobilized carbohydrates by an ELISA (enzyme-linked immunosorbent assay). Of the carbohydrates tested, the eluted antibodies were observed to bind only to those carbohydrates containing α-galactose (Good et al., 1992, Transplant Proc. 24:559–562). A subsequent study examining the cytotoxic effect of human and baboon serum on a pig cell line has shown that carbohydrates containing a terminal α-galactose can neutralize cytotoxicity (Neethling et al., 1994, Transplantation 57:959–963). Additionally, Collins et al., have shown that expression of the Galα1-3Gal antigen in donor organs may be sufficient to bring about the immunological reactions leading to hyperacute xenograft rejection and also that removal of Galα1-3Gal from porcine cells eliminates the binding of 70–80% of xenoreactive antibody (Collins et al., 1994, Xenotransplantation 1:36–46; Collins et al., 1995, J. Immunol. 154:5500–5510).

Recently, the antigenic glycolipid in pig kidney endothelial cells has been identified as a pentasaccharide consisting of Galα1-3Galβ1-4GlcNAcβ1-3Galβ1-4Glc-ceramide (Samuelsson et al., 1994, Immunological Rev. 141:151–168). A study using ELISA and in vitro immunosorbent assays to compare the ability of this αGal pentasaccharide to bind human anti-pig antibodies with that of the αGal disaccharide (Galα1-3Gal) or the αGal trisaccharide (Galα1-3Galβ1-4GlcNAc) has indicated that human anti-αGal antibodies are polymorphic, and that immunoadsorbents containing these αGal oligosaccharides may be capable of removing anti-αGal activity albeit ineffectively (Goldberg et al., 1995, Transplant Proc. 27:249–250). To date, experiments investigating the ability of oligosaccharides containing the αGal epitope to neutralize xenoreactive antibody have been limited to ex vivo hemagglutination, ELISA, and cytotoxicity assays. These limited time frame experiments have demonstrated that the αGal disaccharide (Galα1-3Gal) and αGal trisaccharide (Galα1-3Galβ1-4GlcNAc) are effective in neutralizing the anti-αGal antibody in vitro and that the αGal trisaccharide is ten times more effective than the αGal disaccharide. (Neethling et al., 1996, Transplantation International 9:98–101.)

To date, αGal oligosaccharides longer than the αGal tetrasaccharide have not been tested individually. Further, none of the Galα1-3Gal oligosaccharides have been tested in vivo for the ability to block anti-αGal binding. The ex vivo experiments lack the complexity of the organ xenograft system in vivo and therefore do not contain other variables that might participate in the process of rejection in vivo. Additionally, these experiments have been performed using human serum devoid of cells and it is unclear what role respective pathways play in initiation of the hyperacute rejection, but it is likely that no single pathway alone is entirely responsible. For example, the soluble carbohydrate melibiose (Galα1-6Glu) is a disaccharide similar structurally to Galα1-3Gal that has been shown in vitro to compete with natural αGal epitopes for human Ig binding, however, in vivo administration of this composition has failed to prevent hyperacute rejection and has been found to be cytotoxic to other tissue (Ye et al., 1994, Transplantation 58:330–337). Thus in the absence of evidence to the contrary, hemagglutination and cytotoxicity results cannot reasonably be expected to be predictive of successful xenograft engraftment. The key experiment for modeling human xenotransplantation, the grafting of pig organs into old world monkeys, until now, has not been performed.

While scientific data indicates that most human xenoreactive IgM and some human xenoreactive IgG is specific for the Galα1-3Gal epitope, some human xenoreactive natural antibodies directed against other determinants may also be responsible for hyperactive rejection, as suggested by Parker et al. (1995, Transpl. Immunol. 3:181–191), Lesnikoski et al. (1995, Xenograft endothelial host-mononuclear cell activation and cytokine expression during rejection of pig to baboon discordant xenografts. Abstracts of the XVth World Congress of the Transplantation Society. Transplantation Proceedings) Ye et al. (1994, Transplantation 58:330; and Collins et al., 1994 Xenotransplantation 1:36). Thus far, Galα1-4Gal, Galβ1-3GalNAc, and SO4-3Gal, three other pig carbohydrate specificities to which humans have natural antibodies, have been identified (Holgersson et al., 1990, J. Biochem. 108:766; Holgersson et al., 1991, Glyconj. J. 8:172; and Good et al., 1992, Transplant Proc. 24:559). This possibility is also suggested by the fact that other species such as the pig, goat, dog, rat, etc., which do not produce anti-Galα1-3Gal antibodies have xenoreactive natural antibodies which presumably recognize other structures (Cameron et al., 1983, J. Surg. Oncol. 22:157–163;

Hammer, C. 1989, 21:522–523). Anti-pig antibodies that bind to the protein components on the surface of pig cells have been reported (Tuso et al., Presentation at the American Society of Transplant Surgeons, 12th Annual Meeting in Houston, May 17–19, 1993). It is possible that antibody dependent and other mechanisms are operating through these epitopes independent of the αGal epitope and would be resistant to its inhibitors.

One of the principal concerns of intravenous carbohydrate therapy in xenotransplantation is whether effective xenograft rejection inhibition can be achieved at acceptable non-toxic levels of oligosaccharide. As discussed supra, while ABO-incompatible rejection has been inhibited successfully using intravenous soluble carbohydrates as antibody inhibitors (Cooper et al., 1993, Transplantation 56:769–777), this approach has been unsuccessful in previous pig/primate xenotransplantation where the necessary concentrations of the anti-αGal antibody inhibitor melibiose (Galα1-6 Glc) proved highly toxic. Anti-αGal antibodies are known to bind to αGal oligosaccharides with relatively low affinity (Parker et al., 1995 Transplant Immunology 3:181–191; Parker et al., 1994, J. Immunology 153:3791–3803). This low affinity is believed to necessitate a high concentration of oligosaccharide in the recipient's blood in order to block the binding of circulating anti-αGal antibodies to the transplanted organ and may result in side effects due to the high concentrations of carbohydrate (see, e.g., U.S. Pat. No. 5,560,911). This low binding affinity is also thought to possibly have an adverse impact on extracorporeal immunoaffinity treatment by making the removal of anti-αGal antibodies relatively inefficient (see, e.g., U.S. Pat. No. 5,560,911).

A complicated series of multiple overlapping events contribute to the recognition of vascularized discordant grafts, including binding of preformed natural antibodies, complement activation, activation of the coagulation cascade and endothelial cell activation. Due to these multiple overlapping events, the possible involvement of the antibody-independent alternative pathway, the potential involvement of xenoantibodies other than those specific for the αGal epitope, and the low binding affinity of anti-αGal antibodies for αGal oligosaccharides, one would not reasonably expect that treatment with αGal oligosaccharides would be effective in neutralizing anti-αGal antibodies and even if they were, that such neutralization and/or removal of anti-αGal antibodies would be sufficient to overcome HAR or to attenuate xenograft rejection.

2.3. CURRENT APPROACHES TO OVERCOME XENOGRAFT REJECTION

Other approaches for overcoming HAR are also being explored. These approaches generally aim to genetically engineer pigs so that they do not trigger the rejection reaction, by for example, expressing elevated levels of complement regulatory sequences on the surface of endothelial cells (Langford et al., 1993, Abstract #56, Second International Congress on Xenotransplantation, Cozzi et al., 1993, Abstract #57, Second International Congress on Xenotransplantation), expressing fucosyl transferase that competes with α-galactosyltransferase for acceptors and fucosylates the acceptor moiety (Sandrin et al., 1996, Xenotranspl. 3:134–140 and Sandrin et al., 1995, Nature Med. 1:1261–1267), or by knocking out the gene encoding α-galactosyl transferase. An alternative approach attempts to tolerize prospective human recipients to pig tissues, by for example, inducing immunological chimerism (see e.g., Tanaka et al., 1993, Abstract #122, Second International Congress on Xenotransplantation; Zeng et al., 1992, Transpl. Proc. 24:641; Zeng et al., 1992, Transplantation 53:277; Ricordi et al., 1992, Surgery 112:327; Ildstad et al., 1992, Transplantation 53:815; and Ildstad et al., 1992, J. Exp. Med. 175:147). Additionally, the use of human anti-xenograft, anti-idiotypic antibodies has also been proposed as a means by which to inhibit acute complement-mediated cytotoxicity (see U.S. Pat. No. 5,560,911,). To date, no one has successfully been able to achieve clinically significant attenuation of xenograft rejection in vivo, and it is unlikely that these other approaches will succeed in the near future.

2.4. RETARGETING OF HOST EFFECTOR MECHANISMS

Methods of retargeting host effector mechanisms to targets of therapeutic interest using bispecific agents have been reported in the art (see e.g., Meeting Report of the Second International Conference on Bispecific Antibodies and Targeted Cellular Toxicity, February 1991, Immunol. Today, 12(2):51–54). At the most basic level, any therapeutic antibody can be described as a bispecific agent that retargets host defense mechanisms to a chosen target. The antigen-binding "front" end of an antibody binds the antigenic epitope on a tumor cell, for example, and the Fc "tail" serves to attract and deliver host effector mechanisms, specifically complement or cells that possess receptors for the tail region of the antibody. These receptors, FcR, come in several varieties which bind different antibody populations and are expressed on different cell types (macrophages, neutrophils, natural killer, or NK cells, etc.). The host effector mechanisms are the ones that do the damage: complement forms a "membrane attack complex" comprised of components C5b-C9, which lyses the target cell, while FcR$^+$ cells destroy target cells by either phagocytosis or by perforation of their membrane with lytic molecules (e.g., perforin, granzyme). Many strategies for retargeting cytotoxic cells have involved the use of bispecific conjugates of antibodies in which one antibody is directed against the cytotoxic cell receptor involved in lysis, while the second antibody is directed against a target cell structure, such as, for example, a tumor or viral antigen (see e.g., Donohue et al, 1990, Cancer Res. 50:6508–6514; Van Dijk et al., 1989, Int. J. Cancer, 44:738–743; and Segal et al., 1988, Princess Takamatsu Symp. 19:323–331). The administration of chemically cross-linked bispecific monoclonal antibodies reacting with CD3 on T-cells and with cell-surface antigens selectively expressed by tumor cells has been shown to target T-lymphocytes to neoplastic cells and to significantly decrease the growth of an established tumor in vivo (Garrido et al., 1990, Canc. Res. 50:4227–4232).

Recently, Pouletty has described a conjugate for inactivating target cells in a mammalian host which consists of a ligand for the target cell and a component that binds an endogenous cytotoxic effector system (European patent No. EPO 510949, issued Jan. 22, 1997). Pouletty further discloses methods for using these compounds to inactivate a target cell. Pouletty also describes the use of saccharides, such as the blood group A-trisaccharide antigen, as the effector-binding component of the conjugate and discloses the in vitro lysis of CTL-L2 lymphocytes after incubation with an IL2-blood group A conjugate and human serum containing anti-blood group A antibodies. However, Pouletty does not describe or suggest the use of αGal oligosaccharides as the effector binding component of the conjugate. Nor does Pouletty describe or suggest harnessing the pre-existing anti-αGal antibodies in the human serum as an effector agent for complement-mediated lytic attack. Indeed, Pouletty does not even disclose whether the blood group A antigen effector-binding component of the conjugate is effective in binding the endogenous effector system to form a cell inactivating complex in vivo.

Recently, Lussow et al. have described using an IL2-fluorescein conjugate to target anti-fluorescein antibodies to activated T cells, and thereby deplete the targeted cells in vivo (1996, Transplantation Proc., 28:571–572). Lussow et al. disclose that a IL2-fluorescein conjugate component ratio of 1:1 is critical for preventing clearance of this conjugate from the circulation. While Lussow et al. suggest using the αGal epitope as the effector binding component of the conjugate to harness the hyperactive rejection response and redirect this response to desired targets, this reference does not teach whether any oligosaccharides, let alone oligosaccharides containing αGal epitopes, can actually bind an endogenous effector system in vivo. Further, as discussed above, anti-αGal antibodies are known to bind to αGal oligosaccharides with relatively low affinity and it is doubtful that a monovalent αGal oligosaccharide would bind anti-αGal antibodies in vivo (see e.g., Parker et al., 1994, J. Immunology 153:3791–3803; Parker et al., 1995, Transplant Immunology 3:181–191). Accordingly, Lussow et al., does not provide a reasonable expectation that αGal oligosaccharide-cell ligand conjugates could successfully be used to effectuate complement-mediated lytic attack of targeted cells in vivo.

Citation of a reference hereinabove shall not be construed as an admission that such reference is prior art to he present invention.

3. SUMMARY OF THE INVENTION

The present invention relates to methods for attenuating xenograft rejection of transplant tissue between discordant species. Xenograft rejection is thought to be mediated, in part, by xenoreactive antibodies to a Galα1-3Gal motif ("αGal") containing carbohydrate ligand found on the endothelium of xenogeneic organs to initiate complement activation. The invention is based, in part, on the discovery that administration of oligosaccharides comprising the αGal motif, is sufficient to attenuate xenograft rejection in vivo. Additionally, the Inventors have made the surprising discovery that the oligosaccharide compositions of the claimed invention are effective at competitively inhibiting binding of anti-αGal antibodies to xenografts under physiological conditions at nontoxic concentrations and that other xenoantibodies do not play a determinative role in xenograft survival. Accordingly, the present invention relates to methods for inhibiting anti-αGal antibody binding to donor organ endothelium, by administering an effective amount of a pharmaceutical composition comprising an amount of an αGal oligosaccharide, or a pharmaceutically acceptable derivative thereof, sufficient to bind anti-αGal antibodies so as to competitively inhibit binding of these antibodies to donor organ endothelium, and to thereby attenuate xenograft rejection and/or trauma resulting from anti-αGal antibody-mediated complement activation.

Also described are methods for suppressing lymphocytes bearing anti-αGal idiotypes and for predicting the severity of xenotransplant rejection in human recipients. In preferred embodiments, the administration of compositions comprising αGal oligosaccharides or pharmaceutically acceptable derivatives thereof, that are multivalent or associated with or conjugated to cytocidal agents, targets destruction of B cells bearing surface exposed anti-αGal immunoglobulins (or idiotypes).

Human serum may have up to 1% of IgG and IgM with specificity for the αGal epitope (Galili et al., 1993, Immunol. Today 14:480–482). In one embodiment, compositions comprising αGal oligosaccharides, or pharmaceutically acceptable derivatives thereof, target anti-αGal antibodies to tissue or cell types having a distinguishing surface marker. This method comprises administering a pharmaceutical composition comprising an amount of an αGal oligosaccharide, or a pharmaceutically acceptable derivative thereof, associated with or conjugated to a ligand for a specific cell-surface marker so as to target anti-αGal antibodies to tissue or cells bearing this marker. This method may be applied in humans or old world monkeys to target complement-mediated lytic destruction or phagocytosis of any cells, viruses, or tissue expressing the distinguishing surface marker, including, but not limited to, cells or tissue responsible for autoimmunity disorders, viral diseases, parasitic diseases or immunosuppression.

The αGal oligosaccharide composition may be administered alone or in combination with other agents useful in attenuating xenograft rejection, including conventional non-specific immunosuppressive agents, such as, for example, cyclosporine, cyclophosphamide, methylprednisolone, prednisone, and azathioprine. In a further embodiment, the pharmaceutical compositions comprise an anti-inflammatory and/or antibiotic and/or anti-thrombolytic.

It is a primary object of this invention to provide a method and associated compositions for attenuating xenograft rejection or to alleviate trauma caused by anti-αGal antibody triggered complement-mediated lytic attack by interfering with complement activation resulting from anti-αGal antibody binding to cell surfaces, in particular donor organ endothelium. Accordingly, the pharmaceutical compositions of the invention may be administered alone, together with, or in seriatim with other therapy regimens directed toward reducing binding of xenoreactive antibody in host serum, preferably anti-αGal antibody to donor organ cells or tissue.

Xenoantibodies may be neutralized in vivo, by additional techniques which include, but are not limited to, the administration of human anti-animal anti-idiotypic antibodies, and ex vivo by additional techniques which include, but are not limited to, extracorporeal immunoaffinity treatment with human anti-animal idiotypic antibodies, plasmapheresis, perfusion of recipient blood through donor organs, cells or tissue, and exposure to αGal oligosaccharide compositions of the invention.

In addition to therapeutic methods, the invention also relates to pharmaceutical compositions comprising an amount of αGal oligosaccharide, or a pharmaceutically acceptable derivative thereof, sufficient to competitively inhibit binding of anti-αGal antibodies to donor organ endothelium, and a pharmaceutically acceptable carrier. The invention further relates to pharmaceutical compositions comprising an amount of αGal oligosaccharide, or a pharmaceutically acceptable derivative thereof, effective in targeting anti-αGal antibodies to marked cells or tissue, and a pharmaceutically acceptable carrier.

The compositions of the invention may include any oligosaccharide comprising the αGal motif (i.e., Galα1-3Gal), including but not limited to, the αGal oligosaccharides Galα1-3Gal (αGal disaccharide), Galα1-3Galβ1-4 (Glc or GlcNAc) (αGal trisaccharide), Galα1-3Galβ1-4GlcNAcβ1-3Gal (αGal tetrasaccharide) and Galα1-3Galβ1-4GlcNAcβ1-3Galβ1-4Glc (αGal pentasaccharide) which corresponds to the antigenic glycolipid in pig kidney endothelial cells, or any combination thereof. Other embodiments of the invention are directed to pharmaceutically acceptable derivatives of αGal oligosaccharides.

The αGal oligosaccharides of the invention may be monovalent or multivalent and may comprise one or multiple αGal oligosaccharides. In specific embodiments, the monovalent or multivalent αGal compositions of the invention comprise the αGal disaccharide, trisaccharide, tetrasaccharide and/or pentasaccharide, corresponding to the antigenic glycolipid in pig kidney endothelial cells, or a pharmaceutically acceptable derivative thereof. The αGal oligosaccharide component is optionally associated with or conjugated to biologically inert molecules to enhance (or reduce) stability or biological half-life, reduce toxicity, target cells or tissue and/or to temporarily mask the αGal epitope.

In a particular embodiment of the invention described by way of example in Section 6.7, the ability of the αGal pentasaccharide Galα1-3Galβ1-4GlcNAcβ1-3Galβ1-4Glc to effectively neutralize anti-αGal antibody in vivo and to thereby attenuate xenograft rejection of a pig heart in a baboon recipient is disclosed.

3.1. DEFINITIONS

As used herein, "Gal" refers to galactose; "Glc" refers to glucose; and "GlcNAc" refers to N-acetylglucosamine.

As used herein, the term "αGal oligosaccharide" refers both to compounds comprising the αGal motif (Galα1-3Gal) and to such compounds associated or conjugated with an αGal oligosaccharide as described herein. αGal oligosaccharides are defined herein as organic compounds comprising two or more saccharide moieties in which a galactose moiety is covalently joined by an α1-3 glycosidic linkage to another galactose moiety. αGal oligosaccharides may be referred to with respect to the number of saccharide units corresponding to the antigenic glycolipid in pig kidney endothelial cells, i.e., a disaccharide comprises Galα1-3Gal; an αGal trisaccharide comprises Galα1-3Galβ1-4GlcNAc; an αGal tetrasaccharide comprises Galα1-3Galβ1-4GlcNAcβ1-3Gal; and an αGal pentasaccharide comprises Galα1-3Galβ1-4GlcNAcβ1-3Galβ1-4Glc.

As used herein, "hyperacute rejection" refers to rapid graft rejection, beginning minutes after implantation, and which is mediated by pre-existing antibodies to the graft.

As defined herein, a "xenograft" may be an organ, tissue, aggregates of cells, or cells, collectively referred to herein as "tissue." The tissue may be selected from any appropriate tissue of the body of the tissue donor. These tissues include, but are not limited to, heart, kidney, lung, islet cells, liver, bowel and skin cells.

As used herein, the phrase "attenuation of xenograft rejection" means to inhibit or interfere with processes leading to hyperacute rejection of a xenotransplant. The treatment is considered therapeutic if there is inhibition, delay, or reduction of symptoms associated with hyperacute rejection such as ischemia, thrombosis, myocardial congestion and tissue necrosis.

As used herein, the terms "marked cells" or "cells containing a surface marker" refer to cells expressing a molecule on their surface that allows for targeting of a composition of the invention to the surface of the cells.

The term "pharmaceutically acceptable carrier" refers to a carrier medium that does not interfere with the effectiveness of the biological activity of the active ingredient, is chemically inert and is not toxic to the subject to which it is administered.

As used herein the term "pharmaceutically acceptable derivative" refers to any homolog or analog corresponding to αGal oligosaccharides as described in Section 5.1. infra, which binds anti-αGal antibodies and is relatively non-toxic to the subject to which it is delivered.

The term "therapeutic agent" refers to any molecule, compound or treatment, preferably an anti-inflammatory, anti-thrombolytic and/or antibiotic, that assists in reducing untoward effects resulting from xenotransplantation.

4. BRIEF DESCRIPTION OF THE FIGURES

Figure 1B:
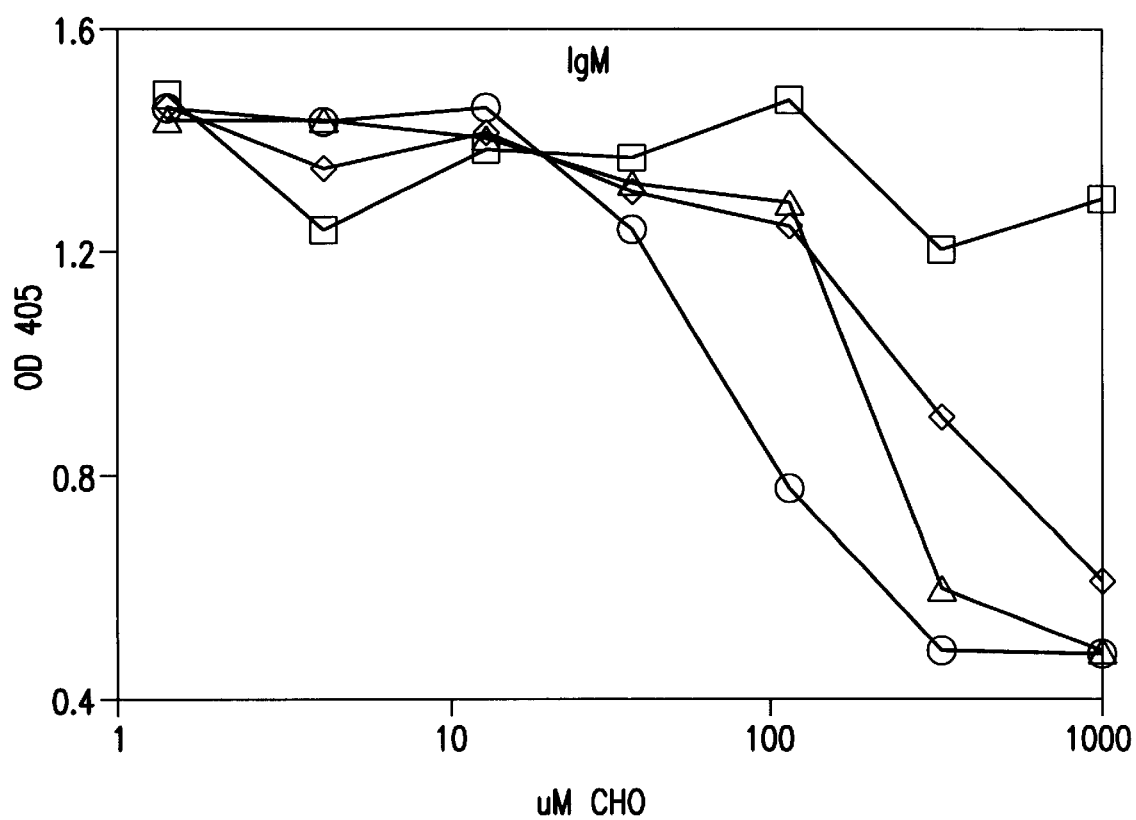

FIGS. 1A–1B In vitro mouse laminin ELISA evaluation of soluble αGal oligosaccharides as neutralizers of anti-αGal antibodies. Immobilized mouse laminin serves as a capture ligand for anti-αGal antibodies. FIG. 1A and FIG. 1B show the extent of anti-αGal IgG and IgM antibody neutralization as a function of αGal oligosaccharide or sucrose concentration ($\mu$M), respectively. Diamonds represent αGal disaccharide; circles represent αGal trisaccharide; triangles represent αGal pentasaccharide; and squares represent sucrose. The binding of anti-αGal antibodies is inhibited to different extent by αGal oligosaccharides of different lengths. The non-αGal oligosaccharide tested does not inhibit antibody binding.

Figure 2A:
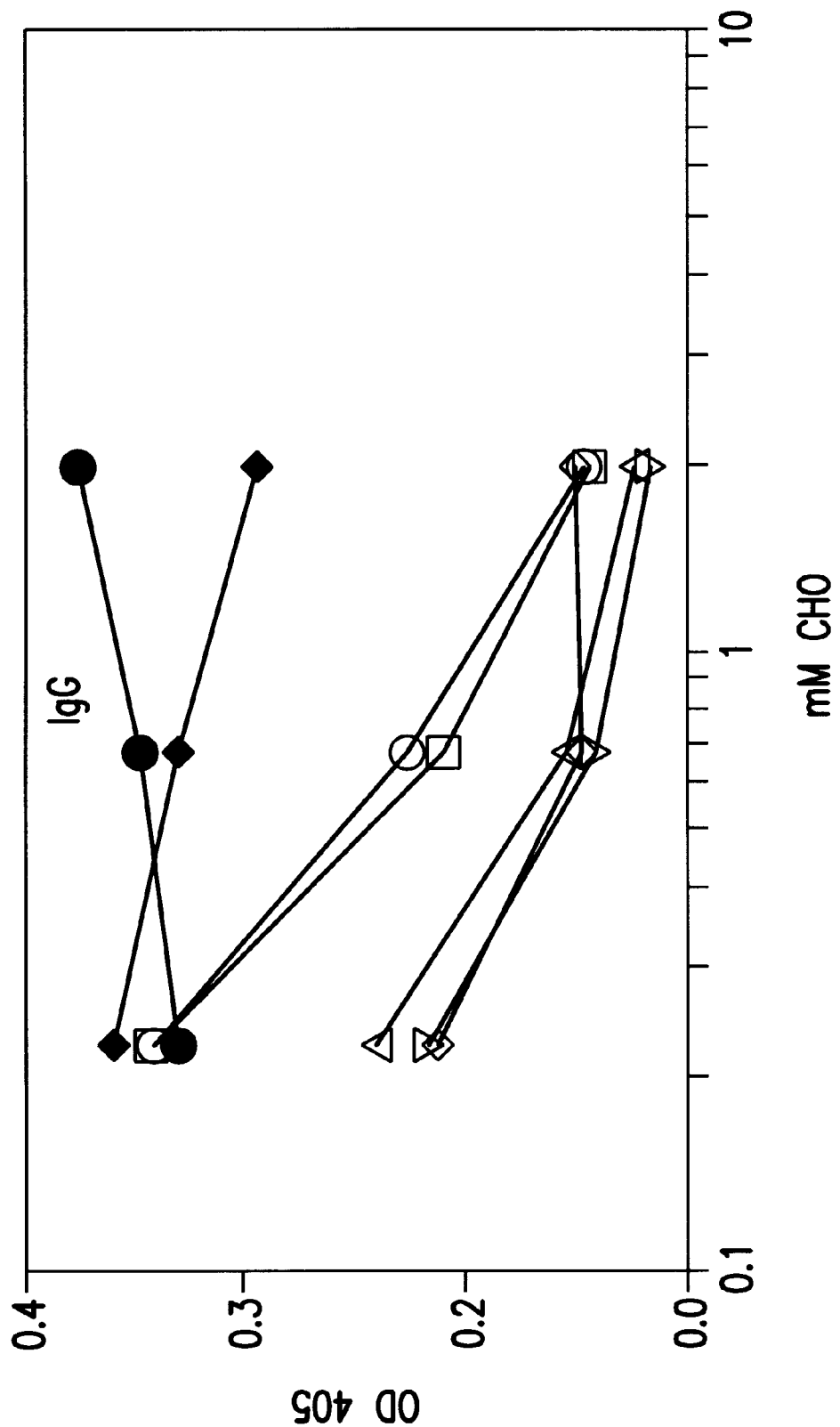
Figure 2B:
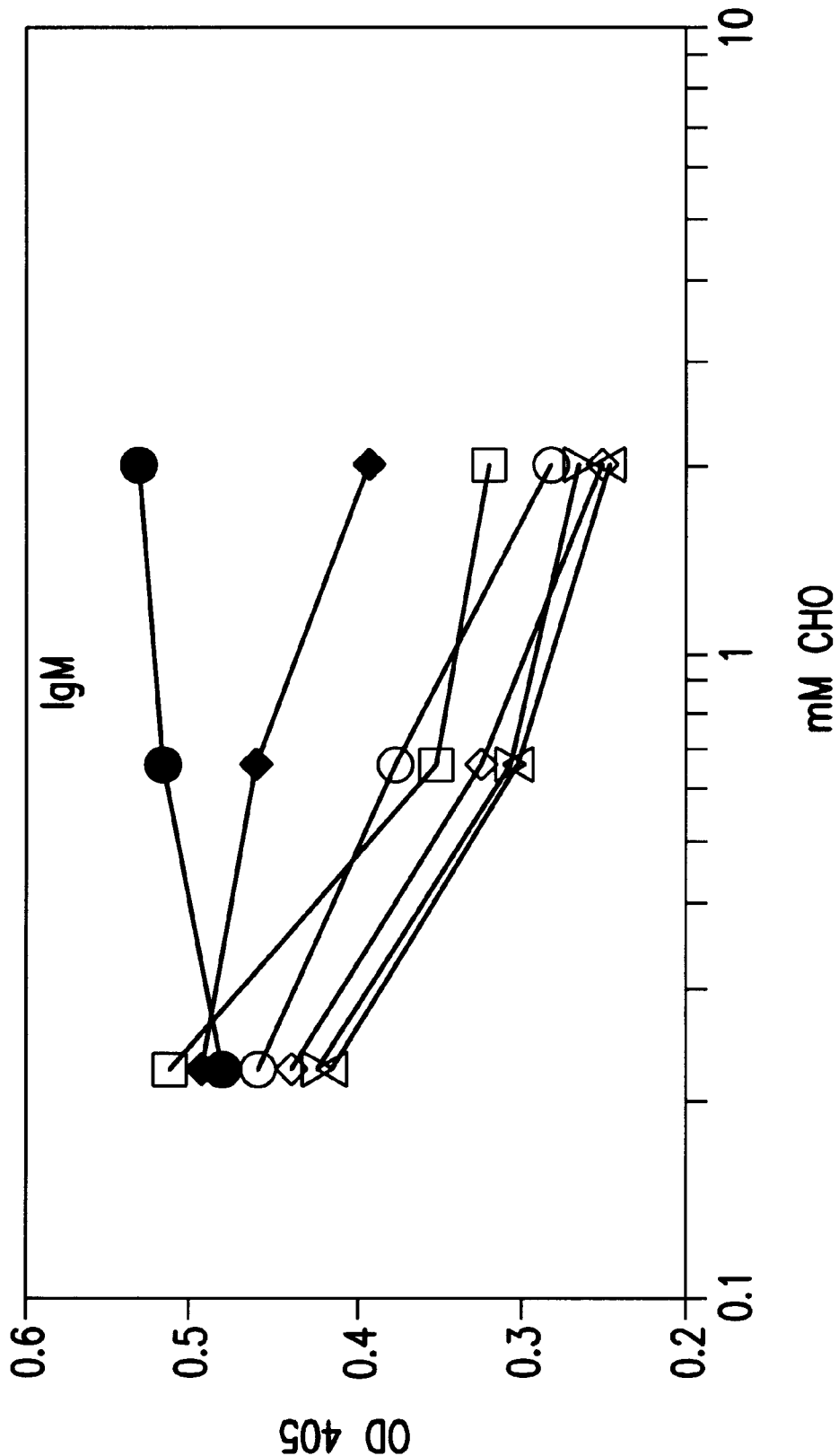

FIGS. 2A–2B In vitro immobilized αGal oligosaccharide ELISA analysis evaluation of soluble αGal oligosaccharides as neutralizers of anti-αGal antibodies. FIG. 2A and FIG. 2B show the extent of anti-αGal IgG and IgM antibody neutralization as a function of soluble αGal oligosaccharide concentration (mM), respectively. Squares represent Galα1-3Gal; shaded diamonds represent Galβ1-4Gal; circles represent Galα1-3Galβ1-4Gal; diamonds represent Galα1-3LacNAc; triangles represent Galα1-3Galβ1-4Galα1-3Gal; inverted triangles represent Galα1-3 LNnT (αGal pentasaccharide); and shaded circles represent sucrose.

Figure 3A:
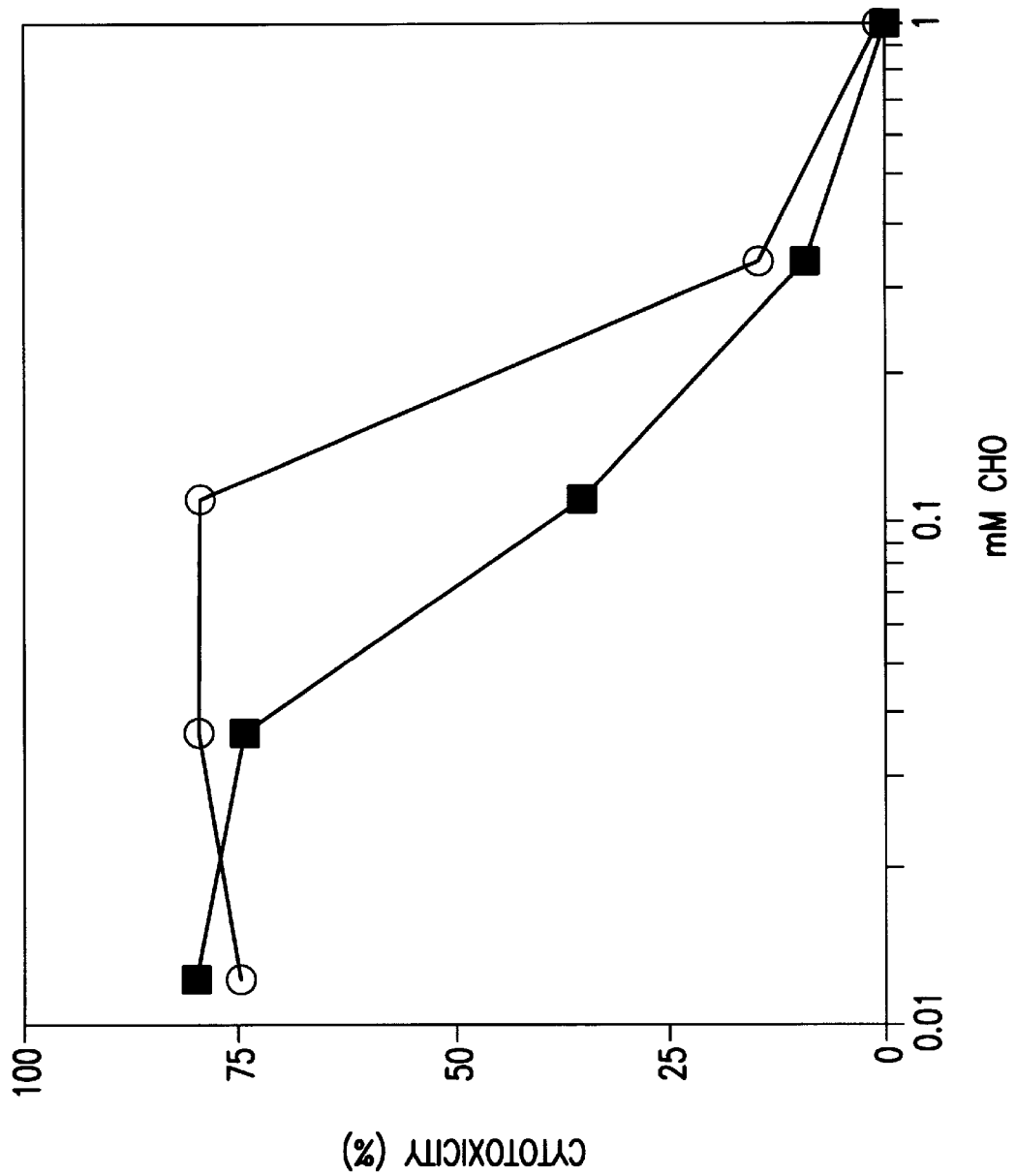

FIGS. 3A–3B In vitro cytotoxicity evaluation of αGal oligosaccharides as neutralizers of anti-αGal antibodies. The extent of pig kidney cell line PK-15 cytotoxicity is shown as a function of soluble αGal oligosaccharide (CHO) concentration (mM). Squares represent αGal trisaccharide (Galα1-3Galβ1-4 Gal) and circles represent αGal pentasaccharide (Galα1-3Galβ1-4Galα1-3Galβ1-4Glc). Cytotoxicity is inhibited slightly better by the αGal trisaccharide than by the αGal pentasaccharide.

FIG. 4 Cytotoxicity of serum from a baboon receiving αGal pentasaccharide (αGal-LNnT) intravenously. Shaded circles represent cytotoxicity of serum as recovered from baboon against mouse endothelial cell line MAE. Other lines indicate varying concentrations of exogenously added αGal-pentasaccharide into cytotoxicity assay. Added concentrations of the αGal pentasaccharide are depicted as follows: 2.0 mM, open circle; 1.0 mM, x; 0.5 mM, diamond; and 0.25 mM, open square. This assay shows that α-Gal pentasaccharide compositions of greater than 1 mM inhibit cytotoxicity, and that αGal-pentasaccharide by itself fully inhibits MAE cell cytotoxicity (similar results were obtained with pig PK15 cells).

Figure 5A:
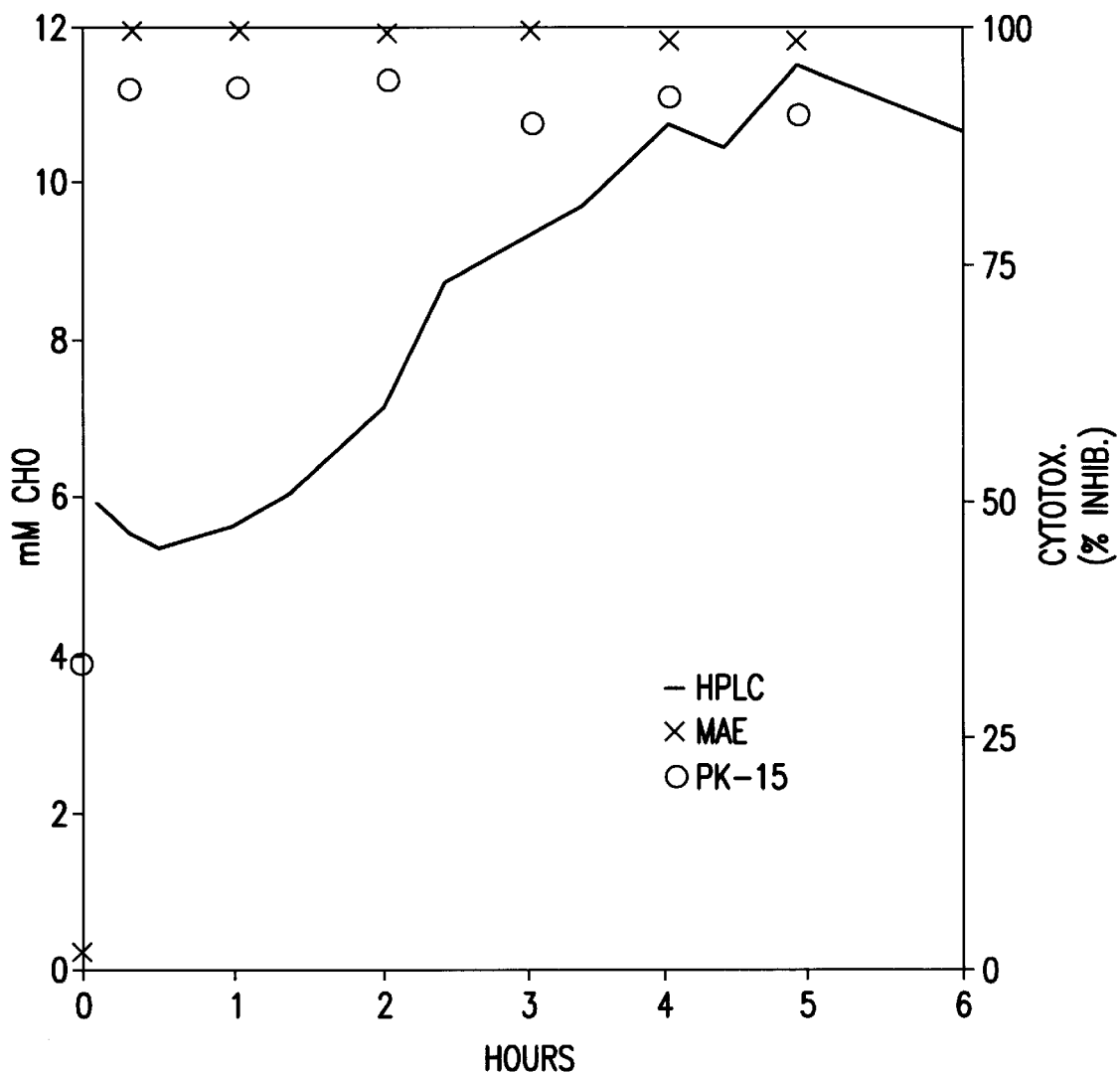
Figure 5B:
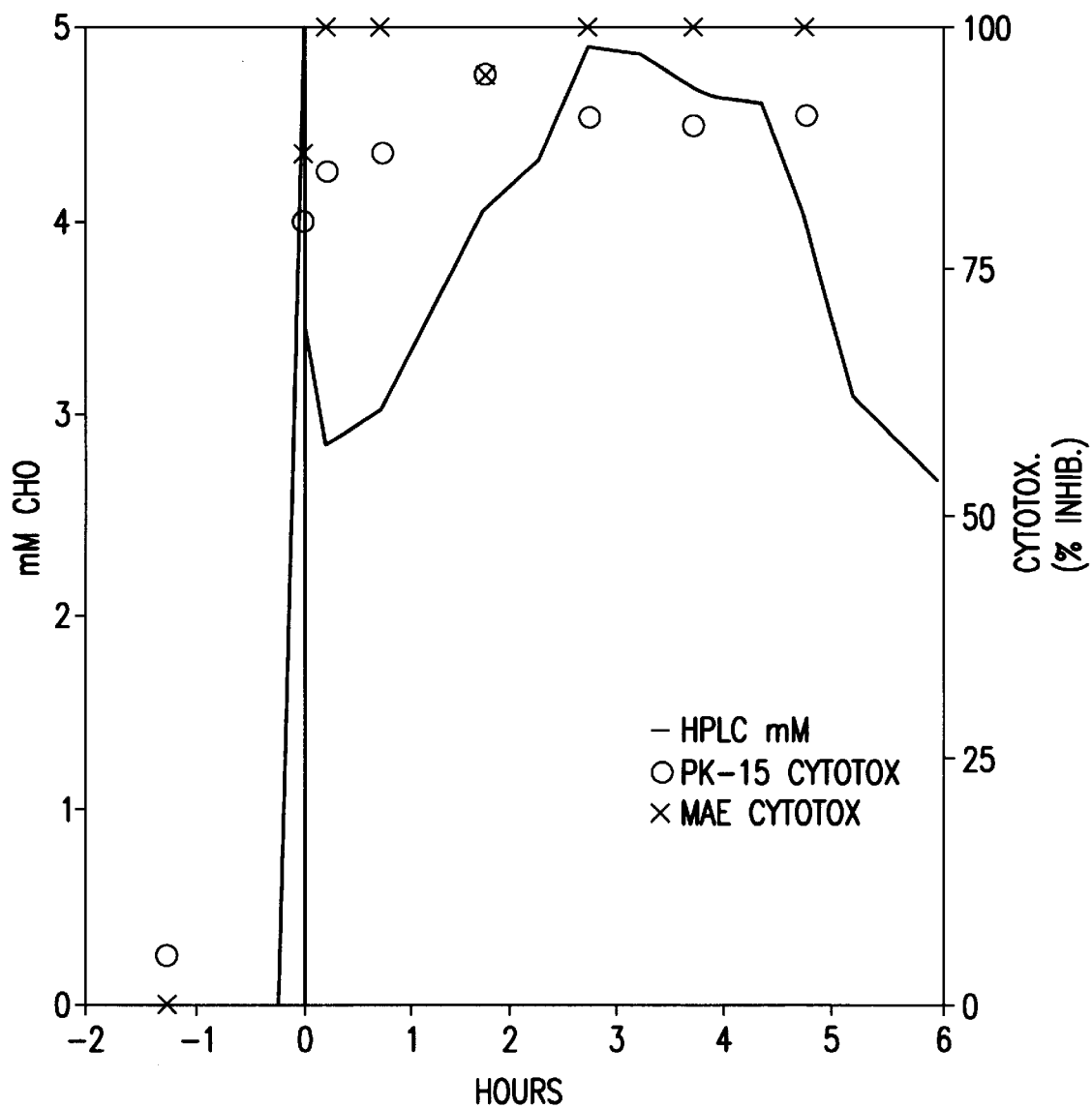

FIGS. 5A–5B Blood αGal pentasaccharide concentration and inhibition of serum cytotoxicity. FIG. 5A, inhibition of cytotoxicity of serum from baboon xenotransplant #1 receiving αGal pentasaccharide intravenously as a function of the plasma concentration of αGal pentasaccharide. FIG. 5B, inhibition of serum cytotoxicity of baboon serum of baboon xenotransplant #2 receiving αGal pentasaccharide intravenously as a function of the plasma concentration of αGal pentasaccharide. The line is αGal pentasaccharide concentration in baboon plasma. Crosses represent % inhibition of cytotoxicity of mouse endothelial cell line, MAE. Circles represent % inhibition of cytotoxicity of pig kidney endothelial cell line, PK-15.

FIGS. 6A–6B Depletion of anti-αGal antibodies from human serum by passage over αGal-sepharose. FIG. 6A, inhibition of serum cytotoxicity of pooled human serum lot

1 passed over αGal trisaccharide (shaded square) and αGal pentasaccharide (open circle). FIG. 6B, inhibition of serum cytotoxicity of pooled human serum lot #2 passed over αGal trisaccharide (shaded square), αGal pentasaccharide (open circle), and glucose (open triangle).

5. DETAILED DESCRIPTION OF THE INVENTION

The invention relates to methods for attenuating xenograft rejection in mammals, including humans and old world monkeys, which comprises administering an amount of an αGal oligosaccharide, or a pharmaceutically acceptable derivative thereof, effective in neutralizing or removing anti-αGal antibodies. The invention also relates to methods of identification, isolation and suppression of lymphocytes bearing anti-αGal idiotypes. The invention additionally encompasses administering an effective amount of an αGal oligosaccharide, or a pharmaceutically acceptable derivative thereof, to target anti-αGal antibody mediated complement activation to cells or tissues containing distinguishing cell-surface markers. The invention further comprises pharmaceutical compositions that may be used in the practice of the invention to attenuate xenograft rejection and/or target anti-αGal directed complement-mediated lytic attack.

The present method provides treatment for attenuating xenograft rejection in humans and old world monkeys, such as for example, in pig to human discordant xenografting. Specifically, the invention provides αGal oligosaccharide compositions, or pharmaceutically acceptable derivatives thereof, capable of competitively inhibiting the binding of preformed host anti-αGal antibodies to xenografts and thereby preventing activation of anti-αGal directed complement-mediated lytic attack of the transferred tissue which leads to hyperacute rejection of the xenograft. The compositions of the invention may be administered alone or in combination with other therapeutic agents, such as, for example, classical immunotherapeutic agents, anti-inflammatories, and/or antibiotics. The invention also encompasses the use of combinations of distinct αGal oligosaccharides, e.g., αGal trisaccharide in combination with αGal pentasaccharide.

The pharmaceutical compositions of the invention may be administered alone, together with, or in seriatim with other therapy regimens directed toward reducing binding of xenoreactive antibodies to donor organ cells or tissue. An example of an in vivo technique that may be used in combination with infusion and/or ex vivo column depletion with αGal oligosaccharide compositions of the invention includes, but is not limited to, infusion with human anti-animal idiotypic antibodies. Examples of ex vivo techniques that may be used in combination with infusion and/or ex vivo column depletion with αGal oligosaccharide compositions of the invention include, but are not limited to, extracorporeal immunoaffinity treatment with human anti-animal idiotypic antibodies, plasmapheresis and perfusion of host blood through donor organs or tissue.

In specific non-limiting embodiments of the present invention detailed in the examples sections infra, anti-αGal antibody neutralization and cytotoxicity studies performed on serum drawn from baboons infused with the αGal pentasaccharide of the invention, are described. Attenuation of xenograft rejection in baboon-pig heart recipients that have been infused with αGal pentasaccharide is also described.

The Inventors have discovered that administration of the αGal oligosaccharides of the invention is effective in achieving significant attenuation of xenograft rejection in. vivo. The methods disclosed herein present the first known successful use of oligosaccharide therapy to attenuate xenograft rejection.

Although described herein with specific reference to pigs, the same compositions and methodology can be used to overcome hyperacute rejection of xenografts from other donor species having a functional α1-3 galactosyl transferase by recipients, such as old world monkeys or humans which do not have a functional α1-3 galactosyltransferase.

5.1. αGAL OLIGOSACCHARIDE COMPOSITIONS

The invention provides pharmaceutical compositions comprising αGal oligosaccharides or pharmaceutically acceptable derivatives thereof, that competitively inhibit binding of anti-αGal antibodies to xenografts. By binding to these antibodies, oligosaccharide compositions of the invention are able to neutralize, remove and/or target anti-αGal antibodies to specific tissue or cell types.

αGal oligosaccharides of the invention include those saccharide compositions comprising two or more saccharide moieties in which a galactose moiety is joined by an α1-3 glycosidic linkage to another galactose moiety. In preferred embodiments the αGal motif (Galα1-3Gal) is located within 15, 10, 5, 4, 3, 2 or 1 saccharide unit(s) from the non-reducing end of the oligosaccharide. In a most preferred embodiment, the αGal motif represents the terminus (i.e., the non-reducing end) of the oligosaccharide. The αGal oligosaccharides may comprise one, or a plurality of αGal motifs. For example, the αGal oligosaccharide may be a branched carbohydrate having multiple terminal Galα1-3Gal residues or a linear oligosaccharide containing both terminal and internal Galα1-3Gal residues.

In preferred embodiments, the αGal oligosaccharides of the invention comprise a saccharide sequence corresponding to the antigenic glycolipid expressed on pig kidney endothelial cell membranes. Such αGal oligosaccharides include, but are not limited to Galα1-3Gal; Galα1-3Galβ1-4GlcNAc; Galα1-3Galβ1-4GlcNAcβ1-3Gal; and Galα1-3Galβ1-4GlcNAcβ1-3Galβ1-4Glc. In a most preferred embodiment, the αGal oligosaccharide is the pentasaccharide, Galα1-3Galβ1-4GlcNAcβ1-3Galβ1-4Glc.

The compositions of the invention also include pharmaceutically acceptable derivatives of αGal oligosaccharides. Such derivatives include but are not limited to salts, pyran ring derivatives, multivalents and conjugates or associations with a αGal oligosaccharide.

In one embodiment, the pharmaceutically acceptable derivatives of αGal oligosaccharides are sulfate substitutes and salts thereof. Suitable cations include alkali metals, alkaline earth metals or ammonium. Any known suitable pharmaceutically acceptable cations may be used, including the cations of conventional non-toxic salts including a metal salt such as an alkali metal salt (e.g., sodium salt, potassium salt, etc.) or an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), a salt with an amino acid (e.g., arginine salt, aspartic acid salt, glutamic acid salt, etc.), and the like.

The pharmaceutically acceptable derivative of the invention may include pyran ring variants in which the oxygen of one or more pyran rings is replaced by another heteroatom. For example, in one embodiment the αGal oligosaccharide derivative comprises an αGal aza sugar in which the oxygen of one or more of the pyran rings is replaced with a nitrogen, to form a piperidine ring system. In another embodiment, the oxygen of one or more of the pyran rings is replaced with a sulfur, to form a tetrahydrothiopyran ring system.

In alternative embodiments, the pharmaceutically acceptable derivative of the invention comprises an αGal oligosaccharide associated or conjugated with a blocking, or masking, agent capable of blocking xenoantibody binding to the αGal oligosaccharide for a predetermined length of time. Suitable blocking agents are known to those in the art and may be removed by natural processes or pharmacological intervention, thereby exposing the αGal epitope. Masking may be achieved by techniques known in the art, including but not limited to, polyacetylation of the αGal oligosaccharide so that serum or administered esterases would de-acetylate and expose the αGal epitope, and capping of one or more terminal αGal motifs with another monosaccharide to alter its antigenic nature, which would be hydrolyzed by a natural or administered glycosidase.

The αGal oligosaccharide of the invention may be associated or conjugated with other molecules. These molecules may be macromolecular carrier groups including, but not limited to, lipid-fatty acid conjugates, polyethylene glycol, protein or carbohydrate. The associated or conjugated molecule may also provide bifunctionality to the αGal oligosaccharide by, for example, targeting αGal oligosaccharides to predetermined tissue or cell types. The association or conjugation between the αGal oligosaccharide and the other molecule may be the result of a direct interaction, such as for example, through a chemical bond or ionic interaction, or alternatively, the association or conjugation with the other molecule may be through a linking group. The linking group can be any group known in the art which serves to link the αGal oligosaccharide, or pharmaceutically acceptable derivative thereof, with the other molecule. Suitable linking groups include saccharides, oligosaccharides, peptides, proteins, $C_{2-20}$ alkyl, oxyalkylene chains or any other group, which does not inhibit the ability of the αGal oligosaccharide component of the composition to bind anti-αGal antibodies. The ability of αGal oligosaccharide components of the composition to bind anti-αGal antibodies may be determined applying assays described in Sections 6.3, 6.4 and 6.5 as well as those known in the art.

The αGal oligosaccharide or pharmaceutically acceptable derivative of the invention may be monovalent or multivalent. Competitive inhibition is typically enhanced by increased valence, as once the first contact has been made, the probability of subsequent contact taking place is favored thermodynamically. The use of multivalents is especially useful in blocking low affinity events where high avidity can compensate. Such is the case for anti-αGal antibodies which, like most anti-carbohydrate antibodies, especially IgM, are of relatively low affinity. The direct correlation between competitive inhibition and valence is demonstrated by BSA glycoconjugates which provide a model for multivalence and which inhibit binding with $IC_{50}$ values in the μM range, as opposed to monovalents which inhibit in the mM range (Simon et al., personal observation). In a specific embodiment, the composition comprises multivalent αGal oligosaccharides or αGal oligosaccharide structures to increase the potency and/or biological half-life of the pharmaceutical. In particular embodiments, the αGal oligosaccharide of the invention is divalent, trivalent, tetravalent, pentavalent, heptavalent or decavalent. In one embodiment, an αGal oligosaccharide (e.g., the αGal tetrasaccharide or αGal pentasaccharide) is found in multiple copies on a compound for use in the invention. In another embodiment, more than one αGal oligosaccharide (e.g., the tetrasaccharide and pentasaccharide) are found in single or multiple copies on a compound for use in the invention. In another embodiment, the oligosaccharide or pharmaceutically acceptable derivative of the invention comprises 2, 3, 4, 5, 10, 20 or 30 αGal motifs on one molecule or is polyvalent.

Multivalent carbohydrates can be prepared using methods known in the art to prepare a branching complex carbohydrate, which conceptually resembles a tree or brush in which each branch or bristle contains a anti-αGal oligosaccharide motif. In preferred embodiments, each branch or bristle is terminated by an αGal motif. Alternatively, monovalent carbohydrates can be associated covalently or noncovalently with a polymer using techniques known in the art (See e.g., Langer et al., International Patent Publication No. WO 94/03184, published Feb. 17, 1994, which is herein incorporated by reference in its entirety). The αGal oligosaccharide or pharmaceutically acceptable derivative thereof may be bound directly or through a linking group to the polymer using known techniques so as to produce a conjugate in which more than one individual molecule of the oligosaccharide is covalently attached. Suitable linking groups include, but are not limited to saccharides, oligosaccharides, peptides, proteins, $C_{2-20}$ alkyl, oxalkylene chains or any other group which does not prevent the anti-αGal antibody binding to αGal oligosaccharide. Suitable polymer supports are compounds with multiple binding sites to the reducing end saccharide or to a terminal end of the linking group which is not bound to the reducing end saccharide, or with multiple binding sites to the $C_1$, glycosidic oxygen of a glucose or N-acetylglucosamine residue. Suitable polymers are known in the art and include, but are not limited to, a polyol, a polysaccharide, avidin, lipids, lipid emulsions, liposomes, a dendrimer, human serum albumin, bovine serum albumin, a protein, polylysine, dextran, a glycosaminoglycan, cyclodextrin, agarose, sepharose, and polyacrylamide.

Multivalent αGal oligosaccharide compositions may be used to neutralize anti-αGal antibodies and/or to target complement-mediated lytic attack to B lymphocytes bearing anti-αGal idiotypes. The construct needed to achieve this effect possesses two or more αGal epitopes on one molecule, or is multivalent. While not wishing to be bound to theory, these compositions would deplete B lymphocytes bearing anti-αGal idiotypes by a mechanism in which one αGal group would be bound by the B-cell's surface immunoglobulin, while the others would be displayed outward, serving as surface ligands for the circulating anti-αGal antibodies. Alternatively, multivalent αGal constructs may down-regulate the production of anti-αGal antibodies by the receptor cross-linking effect described by Dintzis et al. (1990, Eur. J. Immunol., 20:229; U.S. Pat. No. 5,370,871; U.S. Pat. No. 5,126,131; 1976, PNAS, 73:3671–3675; 1990, Immunol. Rev. 115:243–250). In an alternative embodiment, one or more of the αGal epitopes are "masked" by a labile group using known techniques. According to this embodiment, exposed αGal epitopes bind the B-lymphocyte surface immunoglobulin and the masking group is removed gradually by natural or pharmacological intervention, exposing the masked αGal group(s), and bringing about complement-mediated lysis of the B-lymphocytes. The αGal oligosaccharides or pharmaceutically acceptable derivatives of the invention may be masked by masking groups known in the art, including but not limited to acetyl groups that may be deacetylated by serum esterases and thereby expose the αGal epitope; and capping of the αGal motif with a monosaccharide or polysaccharide that alters the antigenic nature of the αGal motif, and which may be hydrolyzed by a natural or administered glycosidase. The ability of masking groups to alter the antigenic nature of the αGal motif and for unmasking to expose the epitope may be routinely determined applying the assays described in Sections 6.3, 6.4 and 6.5.

In another embodiment, the αGal oligosaccharide is chemically linked either directly or through a linker to a cytocidal agent. The αGal oligosaccharide may be chemically linked to any cytocidal agent, using known techniques. Such cytocidal agents include, but are not limited to, toxins (e.g., ricin A, Pseudomonas exotoxin) or cytotoxic drugs (e.g., cytosine arabinoside, daunorubicin). αGal oligosaccharide/cytocidal agent compositions of the invention may be administered to target cytocidal attack of B lymphocytes bearing anti-αGal idiotypes.

The αGal oligosaccharide, or pharmaceutically acceptable derivative of the invention may be associated (e.g., ionic interaction) or conjugated (e.g., covalent linkage) with a ligand for a cell-surface molecule so as to target anti-αGal antibodies to tissue or cells expressing these molecules. Such oligosaccharide-ligand combination may be through the direct interaction of the oligosaccharide and ligand or indirectly using linker means known in the art. The oligosaccharide/ligand combination may be generated by techniques known in the art (See e.g., Stowell and Lee, 1980, Advances in Carbohydrate Chemistry, 37:225–281, which is herein incorporated by reference in its entirety) and are generated so as not to inhibit binding of the αGal oligosaccharide to anti-αGal antibodies. The ability of the αGal oligosaccharide/ligand combination to bind anti-αGal antibody may routinely be determined applying in vitro assays described herein (see Sections 6.3, 6.4 and 6.5) and known in the art. The ability of the αGal oligosaccharide/ligand combination to bind to the cell-surface binding partner of the ligand may be determined using techniques known in the art. The ligand component of the oligosaccharide/ligand combination may comprise monoclonal antibody, cell-surface receptor ligand or other homing molecules for therapeutically significant targets that are known or may routinely be identified and isolated and/or generated using techniques known in the art. For example, for the generation of monoclonal antibodies see generally, Harlow, E., 1988, Antibodies a Laboratory Manual, Cold Spring Harbor, Ed. by Harlow and Lane.

In another preferred embodiment, the αGal oligosaccharide, or pharmaceutically acceptable derivative thereof is associated or conjugated to an autoantigenic peptide for specifically targeting anti-αGal antibodies to the major histocompatibility complex of autoreactive lymphocytes. In other embodiments, the αGal oligosaccharide or pharmaceutically acceptable derivative thereof is associated or conjugated to dominant auto-antigenic peptide epitopes associated with diseases. Such epitopes include, but are not limited to, myelin basic protein peptides in multiple sclerosis, pancreatic islet autoantigenic peptides on p54 in juvenile (type I or autoimmune) diabetes mellitus, acetylcholine receptor peptides in myasthenia gravis, and collagen peptides in rheumatoid arthritis.

In another preferred embodiment, the αGal oligosaccharide or pharmaceutically acceptable derivative thereof is conjugated to an antibody (e.g., monoclonal) for targeting complement-mediated lytic attack to tissue or cell types expressing antigen for the antibody. Since these conjugates localize complement-mediated lytic attack of marked tissue or cell types, the conjugates provide an alternative cidal mechanism to classical antibody-based chemotherapy. Examples of tissue or cell types that may be targeted for complement-mediated lytic attack include tumors which express specific antigens to which antibodies have been developed. In preferred embodiments, the αGal oligosaccharide or derivative is conjugated to the minimal antigen-binding region of a tumor-specific antibody which is identified and generated using techniques known in the art. In other preferred embodiments, the αGal oligosaccharide or derivative is conjugated to single chain antibodies with binding characteristics equivalent to those of the original tumor specific monoclonal antibody. Such single chain antibodies may be selected using antigen-driven screening systems known in the art, (See e.g., McCafferty et al., 1990, Nature, 348:552–554; Clackson et al., 1991, Nature, 352:624–688). These lower molecular weight versions have better vascular access and faster renal clearance than complexes containing the intact monoclonal antibody. Additionally, these truncated antibodies or single chain antibodies contain a smaller number of epitopes than the intact monoclonal antibody, and thereby represent a much weaker immunogenic stimulus when injected into the patient (e.g., human). An intravenous injection of the single chain antibody or truncated antibody is, therefore, expected to be more efficient and immunologically tolerable in comparison with currently used whole monoclonal antibodies (Norman et al., 1993 Transplant. Proc. 25 Suppl. 1:89–93).

In an additional preferred embodiment, the αGal oligosaccharide, or pharmaceutically acceptable derivative thereof, is coupled to a ligand bound by a pathogenic virus or by a virally infected cell. Ligands encompassed by this embodiment include, but are not limited to, CD4-derived peptide bound by gp120 of HIV (from the D1 domain of CD4 and distinct from the MHC-binding region (see e.g., Sakihama et al., 1995, PNAS 92:644–648; and Ryu et al., 1994, Structure 2:59–74), peptides derived from the extracellular domain of chemokine receptors (e.g., CC CKR-5 or fusin) to which the V3 loop of gp120 binds (Choe et al., 1996, Cell 85:1135–1148; Feng et al., 1996, Science 272:872–876), and NeuAcα2-6Galβ1-4Glc ligand for influenza virus, a recessed hemagglutinin ligand which is conserved among the main serotypes of the virus (Connor et al., 1994, Virology 205:17–23; and Suzuki, Y., 1994, Prog. Lip. Res. 33:429–457).

In another preferred embodiment, the αGal oligosaccharide, or pharmaceutically acceptable derivative thereof, is coupled to a ligand that binds targets located on parasites and may be used in the treatment of parasitic diseases. Ligands that target parasitic organisms include, but are not limited to, NeuAcα2-3Gal, the ligand for *Trypanosoma cruzi* (Chagas disease) trans-sialidase, and also for *Plasmodium falciparum* (malaria) adherence to erythrocytes, as well as Gal/GalNAc-terminating oligosaccharides that are bound by *Entamoeba histolytica* surface lectins.

In another preferred embodiment, the αGal oligosaccharide, or pharmaceutically acceptable derivative thereof, is coupled to a ligand that binds targets located on parasites and may be used in the treatment of parasitic diseases. Ligands that target pathogenic organisms may include, but are not limited to, any oligosaccharide motif used by pathogens to recognize host cells which has been described or may be routinely determined through techniques known in the art. Such oligosaccharides have been shown to be effective anti-adhesive agents against pathogens including but not limited to *Bordetella pertussis, Citrobacter freundii, Escherichia coli, Haemophilus influenzae, Helicobacter pylori, Mycoplasma pneumoniae, Proteus mirabilis, Pseudomonas aeruginosa, Salmonella typhimurium, Serratia marcescens, Shigella flexneri, Staphylococcus*

*saprophyticus, Streptococcus mutans, Streptococcus pneumoniae, Streptococcus sanguis, Vibrio cholerae, Cryptosporidium parvum,* and *Entiamoeba histolytica* (See generally Zopf et al., 1996, The Lancet, 347:1017–1021, which is incorporated by reference in its entirety).

In another preferred embodiment, the αGal oligosaccharide, or pharmaceutically acceptable derivative thereof is conjugated to the CD22 ligand NeuAcα2-6Galβ1-4GlcNAc. This conjugate may be used to deliver αGal and thus anti-αGal-mediated complement lytic attack to cells expressing the CD22 molecule which is required for B-T-cell cooperation during lymphocyte activation to regulate immunosuppression.

The αGal oligosaccharide component of the pharmaceutical composition may be administered alone or in combination with other agents useful in attenuating xenograft rejection, including conventional nonspecific immunosuppressive agents, including but not limited to, steroids, cyclosporine, cyclosporine analogs, cyclophosphamide methylprednisone, prednisone, azathioprine, FK-506, 15-deoxyspergualin, and other immunosuppressive agents known in the art. In a further embodiment, the pharmaceutical compositions comprise an antibiotic agent selected from the group consisting of tetracycline, metronidazole, amoxicillin, β lactamases, aminoglycosides, macrolides, quinolones, fluoroquinolones, cephalosporins, erythromycin, ciprofloxacin, and streptomycin. In an additional embodiment, the pharmaceutical composition comprises an anti-inflammatory. Such anti-inflammatories include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, ε-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

5.1.1. αGAL OLIGOSACCHARIDE COMPOSITION PRODUCTION

While, in theory the αGal oligosaccharides of the invention can be purified from biological tissue or cell culture, or produced using classical organic chemistry synthetic techniques known in the art, such derivation of αGal oligosaccharide in the quantity needed according to the methods of the invention, is impractical. Accordingly, it is preferred that the oligosaccharides of the present invention are prepared using enzymatic processes.

Donor saccharide moieties and acceptor moieties for enzymatic synthesis of αGal oligosaccharides may be commercially available and/or may be obtained through organic synthesis applying techniques known in the art. Activated saccharides generally consist of uridine or guanosine diphosphate and cytidine monophosphate derivatives of the saccharides in which the nucleoside mono- and diphosphate serves as a leaving group. Thus, the activated saccharide may be a saccharide-UDP, a saccharide-GDP, or a saccharide-CMP. Nucleoside monophosphates are commercially available, may be prepared from known sources such as digested yeast RNA (see e.g., Leucks et al,. 1979, J. Am. Soc. 101:5829), or routinely prepared using known chemical synthetic techniques (see e.g, Heidlas et al., 1992, Acc, Chem. Res. 25:307; Kochetkov et al., 1973, Adv. Carbohydr. Chem. Biochem. 28:307). These nucleoside monophosphates may then be routinely transformed into nucleoside diphosphates by kinase treatment. For review, see Wong et al., 1994, Enzymes in Synthetic Organic Chemistry, Pergamon Press, Volume 12, pp 256–264.

Glycosyltransferase enzymes for synthesizing the compositions of the invention can be obtained commercially or may be derived from biological fluids, tissue or cell cultures. Such biological sources include, but are not limited to, pig serum and bovine milk. Glycosyltransferases that catalyze specific glycosidic linkages may routinely be isolated and prepared as described in International Patent Publication No. WO 93/13198 (published Jul. 8, 1993), which is herein incorporated by reference in its entirety. Alternatively, the glycosyltransferases can be produced through recombinant or synthetic techniques known in the art (For review, see Wong et al., 1994, Enzymes in Synthetic Organic Chemistry, Pergamon Press, Volume 12, pp 275–279).

The compositions of the invention are preferably synthesized using enzymatic processes (see e.g., U.S. Pat. No. 5,189,674, and International Patent Publication No. 91/16449, published Oct. 31, 1991, each of these references is herein incorporated by reference in its entirety). Briefly, a glycosyltransferase is contacted with an appropriate activated saccharide and an appropriate acceptor molecule under conditions effective to transfer and covalently bond the saccharide to the acceptor molecule. Conditions of time, temperature, and pH appropriate and optimal for a particular saccharide unit transfer can be determined through routine testing; generally, physiological conditions will be acceptable. Certain co-reagents may also be desirable; for example, it may be more effective to contact the glycosyltransferase with the activated sugar and the acceptor molecule in the presence of a divalent cation. Optionally, an apparatus as described by U.S. Pat. No. 5,288,637, is used to prepare such compositions (this reference is herein incorporated by reference in its entirety).

By way of example, the αGal trisaccharide (Galα1-3Galβ1-4GlcNAc) may be synthesized by contacting N-acetylglucosamine with UDP-galactose and a β-N-acetylglucosaminoside β1-4 galactosyltransferase. The product disaccharide is contacted with UDP-galactose and a β-galactoside β1-3 galactosyltransferase, and techniques known in the art are applied to concentrate the resulting trisaccharide (See, for example, Section 6.1).

In another example, the αGal pentasaccharide (Galα1-3Galβ1-4GlcNAcβ1-3Galβ1-4Glc) is synthesized by contacting lactose (galactoseβ1-4glucose) with UDP-N-acetylglucosamine and a galactoside β1-3 N-acetylglucosaminyl transferase. The product trisaccharide is contacted with UDP-Gal and a β-N-acetylglucosaminoside β1-4 galactosyltransferase and the resulting tetrasaccharide is contacted with UDP-galactose and a β-galactoside β1-3 galactosyltransferase. The resulting pentasaccharide is concentrated using techniques known in the art (See, for example, Section 6.2).

While glycosyltransferases are highly stereospecific and substrate-specific, minor chemical modifications are tolerated on both the donor and acceptor components. Accordingly, the oligosaccharide components of the invention may be synthesized using acceptor and/or donor components that have been modified so as not to interfere with enzymatic formation of the desired glycosidic linkage. The ability of such a modification not to interfere with the desired glycosidic linkage may routinely be determined using techniques and bioassays known in the art, such as, for example, labelling the carbohydrate moiety of the activated sugar donor, contacting the acceptor and donor moieties with the glycosyltransferase specific for forming the glycosidic linkage between the donor and acceptor moieties, and determining whether the label is incorporated into the molecule containing the acceptor moiety.

Examples of modified αGal oligosaccharides (i.e., derivatives) encompassed by the invention include, but are not limited to, salts and sulfate substitutes of αGal oligosaccharides, as well as αGal oligosaccharides in which one or more or the pyran rings has been substituted with a piperidine ring system and/or a tetrahydrothiopyran ring system.

αGal oligosaccharide aza sugars in which the oxygen of one or more of the pyran rings of the oligosaccharide is replaced with nitrogen to form a piperidine ring system may be prepared by enzymatic methods known in the art using the appropriate aza saccharide as the acceptor substrate. Alternatively, aza sugar donor moieties may be transferred by the corresponding glycosyltransferase for the natural sugar. Aza glucose can be isolated from natural sources and converted to the aza lactose by the action of a galactosyltransferase in the presence of a galactose donor such as for example, UDP-galactose.

The pharmaceutical composition of the invention may also comprise αGal oligosaccharide thio sugars, in which the oxygen of one or more of the pyran rings of the oligosaccharide is replaced with sulfur to form a tetrahydrothiopyran ring system. The monothiosaccharide may be prepared by known organic chemical techniques from the corresponding monosaccharide and the αGal oligosaccharide derivative thio sugar may be prepared applying enzymatic methods and using the appropriate thio saccharide as the acceptor substrate.

The αGal oligosaccharide or pharmaceutically acceptable derivative thereof, is optionally associated with or conjugated to other molecules, including but not limited to biologically inert molecules, proteins (e.g., monoclonal antibodies), glycoproteins, lipids, glycolipids, and carbohydrates. This association or conjugation may be the result of a direct interaction between the reducing end of the αGal oligosaccharide and the other molecule through an ionic or chemical bond. Alternatively, a linking group may mediate this association or conjugation.

The chemistry necessary to link the reducing end of the αGal oligosaccharide with the other molecule or with the linking group intermediary and to link the αGal oligosaccharide-linking group complex to the other molecule is well known in the field of linking chemistry. For example, a bond between the reducing end saccharide and a linking group can be formed by reacting an aldehyde or carboxylic acid at $C_1$ of the reducing end saccharide or any aldehyde or carboxylic acid group introduced onto the reducing end saccharide by oxidation, with the linking group, to form a suitable bond such as —NH—, —N(R') where R' is $C_{1-20}$ alkyl, a hydroxyalkylamine, an amide, an ester, a thioester, a thioamide.

Additionally, the bond between the reducing end saccharide and the linking group can be formed by reacting the $C_1$ hydroxyl group, in the pyranose form, with an acylating agent and a molecular halide, followed by reaction with a nucleophile to form a suitable bond such as NH—, —N(R')— where R' is $C_{1-20}$ alkyl, —S— and —O—. This type of linking chemistry is further described by Stowell et al, 1980, Advances in Carbohydrate Chemistry and Biochemistry, 37: 225–281.

The oligosaccharide portion can be bound directly to the other molecule (e.g., multivalent support) via the free anomeric carbon of the reducing end saccharide. Alternatively, the reducing end saccharide can be bound via a phenethylamine-isothiocyanate derivative as described by Smith et al., (1978, Complex Carbohydrates part C, Methods in Enzymology, Ed by V. Ginsburg, Volume 50, pp 169–171 or a glycine amine derivative as described in Section 6.4.).

In a specific embodiment, αGal oligosaccharides associated or conjugated with monoclonal antibodies, or fragments thereof, target complement-mediated lytic attack to tissue or cell types expressing the antigen recognized by the monoclonal antibody. Techniques for identifying monoclonal antibodies which recognize a specific cell-surface antigen are known in the art. See generally, Harlow, E., 1988, Antibodies a Laboratory Manual, Cold Spring Harbor, Ed. by Harlow and Lane.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against a distinguishing antigen of interest. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.2. ASSAYS FOR COMPETITIVE INHIBITION OF ANTI-αGAL ANTIBODY BINDING BY αGAL OLIGOSACCHARIDE COMPOSITIONS

The invention is based in part on the discovery that administration of oligosaccharides containing the αGal motif in sufficient quantities to bind to and neutralize anti-αGal antibodies is sufficient to attenuate xenograft rejection of pig to old world monkey/human xenografts in vivo. Thus, the ability of compositions comprising αGal oligosaccharides or pharmaceutically acceptable derivatives thereof to remove, bind, and/or neutralize anti-αGal antibodies is indicative of the ability of the composition to attenuate xenograft rejection.

Quantification of circulating anti-αGal antibodies in the serum of an individual and the ability of compositions comprising αGal oligosaccharides or pharmaceutically acceptable derivatives thereof to remove, bind, and/or neutralize anti-αGal antibodies can be routinely determined applying the immunoassays described in Sections 6.3, 6.4, 6.5 as well as other immunoassays known in the art which may be routinely adapted for such determination. Such immunoassays, include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays (e.g., hemagglutination), complement-fixation assays, immunoradiometric assays, fluorescent immunoassays and protein A immunoassays. These assays may further be applied to determine the dosage of the αGal oligosaccharide composition of the invention to be administered (see Section 5.6.2) and to monitor the neutralization and/or removal of anti-αGal antibodies by the αGal oligosaccharide compositions of the invention.

Immunoassays known in the art may also be routinely odified to determine the affinity of cell surface ligand components of the compositions of the invention (e.g., monoclonal antibodies) to bind to their cell-surface bonding partners.

While assays for measuring circulating anti-αGal antibodies can be accomplished by various immunological methods, ELISA assays have the advantage in that they can be standardized for the immobilized ligand, are reproducibly quantitative, and can be scored for different immunoglobulin isotypes by the use of appropriate secondary detection reagents. ELISA capture ligands for testing human or old world monkey serum antibodies can employ fixed cells, glycolipids, glycoproteins, or oligosaccharides. Such capture ligands include but are not limited to mouse laminin (see Section 6.3), PK-15 pig kidney cells (see Section 6.5), immobilized BSA-αGal neoglycoconjugates, and immobilized αGal oligosaccharides (see Section 6.4). Covalent immobilization of a specific αGal oligosaccharide(s) onto the ELISA immobilized surface, using techniques known in the art, permits the predetermined deposition of known antigenic ligands by covalent chemistry. In addition to determining the ability of αGal oligosaccharides or pharmaceutically acceptable derivatives thereof to bind to and/or neutralize anti-αGal antibodies, such an ELISA is also useful in clinical monitoring of anti-αGal antibodies in blood of patients in advance of, and following xenotransplantation of organs from animals that express the αGal epitope.

Generally, an ELISA assay may comprise contacting serum isolated from a patient, using techniques known in the art, with anti-αGal antibody ligand, in the presence or absence of an αGal oligosaccharide or pharmaceutically acceptable derivative of the invention, under constant conditions. After washing away excess serum, the extent of anti-αGal antibody binding to the ligand is assessed using techniques known in the art, including, but not limited to, adding a secondary antibody with a reporter group (e.g., goat anti-human IgG-alkaline phosphatase), followed by a suitable read-out reagent (e.g., alkaline phosphatase substrate p-nitrophenyl phosphate, or pNPP). Reduced levels of anti-αGal antibody capture by the ligand in serum treated with αGal oligosaccharides of the invention or pharmaceutically acceptable derivatives thereof relative to control samples extracted from the patient prior to or in the absence of treatment with the αGal oligosaccharide or pharmaceutically acceptable derivative of the invention, indicates that the αGal oligosaccharide or pharmaceutically acceptable derivative thereof competitively inhibits binding of anti-αGal antibodies to the αGal motif containing ligand.

In a specific embodiment, αGal oligosaccharide glycine amide derivatives are synthesized by linking glycine to the reducing monosaccharide. The glycine derivative is then applied, under.alkaline conditions, to microtiter plate wells that have been derivatized with N-oxysuccinimide groups. The reduced amino groups displace the succinimide group forming a stable covalent bond. The plate is then blocked with a solution containing non-glycosylated protein (e.g., albumin) to reduce non-specific binding to plastic and test sera or plasmas in the presence or absence of an unbound α-Gal oligosaccharide or pharmaceutically acceptable derivative of the invention, are added to the plate and incubated for an interval to permit attachment of antibodies to the bound oligosaccharide derivatives. After washing the plate repeatedly with blocking solution (containing albumin and detergent), a secondary antibody with a reporter group (e.g., goat anti-human IgG-alkaline phosphatase) is added and allowed to bind the anti-αGal immunoglobulins adsorbed onto the immobilized oligosaccharide. After washing the plate again, a suitable read-out reagent (e.g., alkaline phosphatase substrate p-nitrophenyl phosphate, or PNPP) is then added and color development is measured using a microtiter plate reader.

The addition of serial dilutions of sera in the ELISA assays permits the determination of reactive antibody titers, which can serve to quantitate the circulating anti-αGal activity. In sera drawn from patients treated with soluble oligosaccharide only the unblocked immunoglobulin is free to bind the immobilized ligand (with the caveat that competition for the antigen-binding site of the antibody can result in the displacement of soluble oligosaccharide by immobilized ligand displaying greater affinity or activity). Specific immunoglobulin isotypes can be monitored by using appropriate reagents, e.g., anti-human IgG or IgM.

In another embodiment, quantification of anti-αGal antibodies and/or the extent of xenoreactive antibody neutralization or removal upon treatment with the αGal oligosaccharides of the invention is measured using a cell cytotoxicity assay such as that described in Section 6.5. Such an assay may comprise contacting serum, isolated from a patient using techniques known in the art, with αGal expressing cell monolayers (e.g., pig kidney cells (PK-15), pig aortic endothelial cells, and mouse aortic endothelial cells (MAE). Preferably, these cells are from the same species as the donor and most preferably from the same tissue-type as the tissue to be transplanted), in the presence or absence of an αGal oligosaccharide or pharmaceutically acceptable derivative of the invention, under constant conditions, such as, for example, 1 hour at 37° C. According to this assay, cytotoxicity is mediated by either endogenous complement, or the sera are heat inactivated (e.g., through heating the sera at 56° C. for 30 minutes) and exogenous complement (e.g., from rabbit or guinea pig) is added. After washing away excess serum, the cells are treated with viable dye mix "live-dead" (calcein AM/ethidium homodimer) which is commercially available in the form of a Live/Dead cytotoxicity kit (Molecular Probes Inc., Eugene, Oreg.) and scored for viability using fluorescence microscopy. Staining with the "live/dead" dye mix allows for clear distinction between live cells, which show cytoplasmic green fluorescence and dead cells, which show dark cytoplasm and red fluorescent nuclei. The extent of cell lysis that is complement-mediated may be determined by comparing the results observed in the control for which there has been no inactivation of complement, with the lysis observed with complement that has been inactivated through heat treatment.

The invention also encompasses animal-based model systems, which may include baboon, other old world monkeys, or other animals having serum that contains anti-αGal antibodies. Such animal models may assess the ability of compositions containing an αGal oligosaccharide or pharmaceutically acceptable derivative as an active ingredient to bind to and/or neutralize anti-αGal antibodies, attenuate the rejection of a xenotransplant expressing the αGal epitope and/or to suppress B lymphocytes expressing anti-αGal idiotypes. Generally, this assay may involve exposing animal models to a compound containing an αGal oligosaccharide or pharmaceutically acceptable derivative as an active ingredient, at a sufficient concentration and for a time sufficient to elicit the desired effect in the exposed animals. The response of the animals to the exposure may be monitored by assessing the level of anti-αGal reactive antibodies in the serum of the animal, evaluating the appearance of the xenografted organ, and/or quantitating B lymphocytes expressing anti-αGal idiotypes. Dosages of test agents may be determined by deriving dose-response curves, as discussed in Section 5.6.1, below.

The assays described herein may be applied to routinely determine which αGal oligosaccharides, or pharmaceutically acceptable derivatives thereof, are able to bind and thereby neutralize and/or remove anti-αGal antibodies and the optimal concentrations for doing so. The assays may also be applied to determine the relative binding affinity for anti-αGal demonstrated by the αGal oligosaccharide compositions of the invention. Once αGal oligosaccharides, or pharmaceutically acceptable derivatives displaying the greatest binding affinity have been identified, these compounds are optionally combined and the assays are routinely applied to determine optimal combination concentrations for the pharmaceutical compositions of the invention.

Applying these assays, the relative anti-αGal binding activity that a αGal oligosaccharide or pharmaceutically acceptable derivative exhibits against the anti-αGal antibody profile of the serum of an individual may be determined and the αGal oligosaccharide and/or pharmaceutically acceptable derivative combination formulation best suited for neutralizing and/or binding the anti-αGal profile of an individual can be determined (see Section 5.3).

The αGal oligosaccharide or pharmaceutically acceptable derivative thereof may then be combined with suitable pharmaceutically acceptable carriers and administered by techniques known in the art, such as those described in Section 5.6 infra.

Other methods for assaying the extent of xenoreactive antibody neutralization and/or removal will be known to the skilled artisan and are within the scope of the invention.

5.3. FORMULATION OF PATIENT SPECIFIC PHARMACEUTICAL COMPOSITIONS

The human body produces anti-αGal antibodies in response to common bacterial antigens present in gastrointestinal and respiratory systems (Galili et al., 1988, Infection and Immunity, 56(7):1730–1737). The variability of intestinal and respiratory bacterial flora, as well as the diversity of immune response among individuals, suggests the existence of subpopulations and variable profiles of anti-αGal antibodies in potential recipients.

In particular embodiments, the invention provides methods for formulating a pharmaceutical composition which comprises αGal oligosaccharides and/or pharmaceutically acceptable derivatives thereof that are able to competitively inhibit binding of the anti-αGal antibody profile of an individual. Such methods are achieved by withdrawing serum from the individual using techniques known in the art and testing the ability of a panel of αGal oligosaccharides, or pharmaceutically acceptable derivatives thereof, to determine which particular αGal oligosaccharides or derivatives competitively inhibit anti-αGal binding to donor endothelium (or cell lines such as PK-15 pig kidney cells, pig aortic endothelial cells, or MAE mouse aortic endothelial cells). Preferably, these cells are from the same species as the donor and most preferably from the same tissue-type as the tissue to be transplanted). The αGal oligosaccharides thereby identified as having the highest activity in inhibiting the binding of anti-αGal antibodies in the patient's serum are then used as components of an ex vivo depletion device or as a pharmaceutical composition comprising them to treat the patient.

The ability to formulate a therapeutic composition to contain only αGal oligosaccharides or pharmaceutically acceptable derivatives thereof, demonstrating high activity in neutralizing the anti-αGal antibody profile of a patient minimizes the dosage of antibody-neutralizing oligosaccharide to be delivered. This ability to formulate a therapeutic composition to contain only those αGal oligosaccharides or pharmaceutically acceptable derivatives thereof demonstrating high activity in inhibiting binding of anti-αGal antibodies to donor endothelium is extremely valuable since the risk of side effects increase with the concentration of the αGal oligosaccharide or pharmaceutically acceptable derivative thereof.

Tissue sources and cell lines expressing cell-surface antigens recognized by anti-αGal antibodies are readily available. For example pig kidney cells (PK-15, ATCC CCL 33, Rockville, Md.) and pig aortic endothelial cells (AG 08472, N.I.A. Aging Cell Culture Repository, Camden, N.J.) are available from cell culture repositories. In one embodiment, potential recipient serum is tested in assays, such as those described infra, for the ability to bind to and optionally to kill cells expressing cell-surface antigens recognized by anti-αGal antibodies in the presence of αGal oligosaccharides or pharmaceutically acceptable derivatives thereof. αGal oligosaccharides and pharmaceutically acceptable derivatives thereof found to be effective in inhibiting binding of the anti-αGal antibodies to the cells are preferably then tested over a range of concentrations using techniques known in the art. In a specific embodiment of the invention, the pharmaceutical composition of the invention comprises a plurality of αGal oligosaccharides and pharmaceutically acceptable derivatives thereof determined to be effective in neutralizing binding of the recipient's anti-αGal antibody profile to cells expressing cell surface antigens recognized by anti-αGal antibodies. In particular embodiments, the pharmaceutical composition comprises 2, 3, 4, 5, 6, 7, 8, 9, or 10 distinct αGal oligosaccharides or pharmaceutically acceptable derivatives thereof determined to have activity in neutralizing the anti-αGal antibody profile of the recipient.

The invention therefore provides methods by which to identify αGal oligosaccharides and pharmaceutically acceptable derivatives thereof that neutralize the anti-αGal antibody profile of a potential recipient, and by which pharmaceutical compositions containing these αGal oligosaccharides and pharmaceutically acceptable derivatives alone or in combination are routinely formulated. The invention further provides methods for treating or preventing hyperacute rejection of xenografts in humans and old world monkeys, by administering the pharmaceutical compositions of the invention.

The invention thus provides methods for formulating on a patient-to-patient basis, a pharmaceutical composition comprising αGal oligosaccharides or pharmaceutically acceptable derivatives thereof that are known to be effective in neutralizing the anti-αGal antibody profile in an individual. Accordingly, the αGal oligosaccharides of the invention may be administered alone or in combinations for effectively neutralizing different anti-αGal antibody profiles. The in vitro assays described in Sections 5.2, 6.3, 6.4 and 6.5 may be applied to assess the ability of the α-Gal oligosaccharide compositions of the invention to bind the anti-αGal profiles of different potential recipients.

5.4. DIAGNOSTIC USES OF THE αGAL OLIGOSACCHARIDE COMPOSITIONS OF THE INVENTION

The present invention is based in part on the discovery that the ability to neutralize anti-αGal antibody directed complement-mediated lytic attack is determinative of whether a xenograft will be accepted. Accordingly, concentrations of these antibodies and/or B-lymphocytes bearing anti-αGal idiotypes are likely to approximate the severity of xenograft rejection.

The concentration of anti-αGal antibodies in the serum of a potential recipient is likely to have a direct correlation with the severity in which the recipient will reject a xenograft, i.e., the higher the concentration of these antibodies in the serum of an individual, the more severe the rejection of a xenograft. Quantification of anti-αGal antibody concentrations in the serum of a potential recipient may also aid in designing an effective therapy regimen for the patient. Assays described infra (Sections 5.2, 6.3, 6.4 and 6.5) and known in the art may be applied to determine the concentration of anti-αGal antibodies in the serum of a potential recipient.

The number of lymphocytes bearing anti-αGal idiotypes in a potential recipient may also be used as a predictor of the severity of xenograft rejection. A high number of lymphocytes bearing anti-αGal idiotypes is likely to be associated with a more severe rejection of a xenograft, as well as faster regeneration of anti-αGal antibodies. Methods for quantifying lymphocytes bearing anti-αGal idiotypes in a potential recipient are known to those in the art. B-lymphocytes including those bearing anti-α-Gal idiotypes may be isolated from lymph nodes (via lymph node aspirate or biopsy) or peripheral blood using techniques known in the art, such as, for example, (+) or (−) selection by immunomagnetic beads (Dynal, A. S. Norway).

One method of quantifying B-lymphocytes bearing anti-αGal idiotypes involves isolating mononuclear cells from patients' peripheral blood by the histopaque method (Sigma, St. Louis, Mo.). According to this method, the cells are incubated with an αGal oligosaccharide composition coupled with fluorescein isothiocyanate using techniques known in the art in order to visualize cells with the surface-expressed idiotype. In addition to the FITC-labeled αGal oligosaccharide composition (green fluorescence), the cells are also stained with PerCP-labeled (red fluorescence) B-lymphocyte-specific monoclonal antibody Anti-Leu 12 (Becton Dickinson, San Jose, Calif.). This double staining procedure is followed by fluorescence analysis with Becton/Dickinson's FACScan using the two-color program. The subsets of B-lymphocytes bearing specific anti-αGal idiotypes can then be accurately counted.

5.5. THERAPEUTIC USES OF THE αGAL OLIGOSACCHARIDE COMPOSITIONS OF THE INVENTION

The presence of xenoantibodies comprises the principal, and most devastating, problem in attempts to xenotransplant animal organs into humans and old world monkeys. For example, pig hearts transplanted into baboons or cynomologous monkeys turn dark and necrotic in as little as 5–10 minutes following vascular connection, a phenomenon known as hyperacute rejection (HAR). It has been estimated that a 1–2 week regimen of xenoantibody neutralization or removal would overcome the hyperacute rejection barrier. Evidence to support this concept arises from experience with ABO-mismatched organ transplants (Cooper et al., 1993, Transplant. 56:769–777; Alexandre et al., 1987, Transplant Proc. 19:4538; and Bennett et al., 1987, Transplant Proc. 19:4543). According to this concept, after the hyperacute rejection barrier has been overcome, an "accommodation" takes place and the organ can be stabilized with routine immunosuppression regimens directed to suppressing cellular rejection (Bach et al., 1991, Transplant. Proc. 23:205; Simpson et al., 1989, Xenograft, Elsevier, N.Y., 25:273–284; Michler, 1987, Transplantation 44(5)632–636).

The majority of xenoantibodies present in the blood of humans and old world monkeys recognize an antigenic epitope on donor vascular epithelium containing a αGal motif (Galα1-3Gal). The present invention is based in part on the discovery that binding of anti-αGal antibodies to donor endothelium and the complement-mediated lytic attack directed thereby, are the determining factors leading to hyperacute rejection of xenografts and that removal or neutralization of anti-αGal antibodies attenuates xenograft rejection. Accordingly, the invention relates to methods which utilize αGal oligosaccharide compositions to interfere with (i.e., competitively inhibit) the ability of anti-αGal antibodies to bind to donor organ endothelium. According to the invention, αGal antibody neutralization or depletion may be achieved through either or both in vivo and ex vivo treatment of host serum or serum to be administered to the host.

In one embodiment, anti-αGal antibodies are depleted by passing blood to be administered to a patient over αGal oligosaccharides or pharmaceutically acceptable derivatives of the invention that have been bound either directly or through a linker, to a biocompatible solid support using methods known in the art, including, but not limited to those techniques described in Sections 5.1.1 and 6.4. According to this embodiment, blood of the patient is passed ex vivo over the αGal-support matrix complex and then transfused into the patient using techniques known in the art. Extracoporeal reactors, such as dialysis or plasmapheresis machines, are readily adapted for this procedure by methods known in the art.

A preferred method of neutralizing anti-αGal antibodies involves the intravenous administration of αGal oligosaccharide(s) or pharmaceutically acceptable derivative(s) thereof in sufficient quantity to block binding of the circulating antibody to the donor endothelium and thereby prevent anti-αGal antibody directed complement-mediated lytic attack of the transplanted tissue. Methods and compositions for formulating and administering the pharmaceutical compositions of the invention are known in the art, and include but are not limited to that described in Sections 5.2, 5.3 and 5.6 infra.

Assays which can be used to determine whether administration of a specific composition attenuates xenograft rejection are discussed infra (see, Sections 5.2, 6.3, 6.4 and 6.5). These assays can indicate which αGal oligosaccharide or pharmaceutically acceptable derivative thereof has the desired therapeutic efficacy in attenuating xenograft rejection and additionally may be applied to assay for the ability of combinations of αGal oligosaccharides and/or pharmaceutically acceptable derivatives to competitively inhibit binding of anti-αGal antibodies to the endothelium of the donor organ.

The αGal oligosaccharide compositions of the invention may be administered alone or in combination with other therapeutic agents, including but not limited to, antibiotics, steroidal and non-steroidal anti-inflammatories, and conventional immunotherapeutic agents. Conventional nonspecific immunosuppressive agents, that may be administered in combination with the αGal oligosaccharide compositions of the invention include, but are not limited to, steroids, cyclosporine, cyclosporine analogs, methylprednisolone, and azathioprine FK-506, 15-deoxyspergualin, and other immunosuppressive agents that act by suppressing the function of responding T cells. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the agents given first, followed by the second. The invention also encompasses the use of a combination of distinct αGal oligosaccharides, e.g., αGal trisaccharide in combination with αGal pentasaccharide.

In a specific embodiment, the therapeutic method of the invention is carried out as monotherapy, i.e., as the only agent provided for attenuating xenograft rejection. In preferred embodiments, this therapy involves delivery of αGal trisaccharide and/or αGal pentasaccharide.

It is a primary object of this invention to provide a method and associated compositions for attenuating xenograft rejection or to alleviate trauma caused by anti-αGal antibody directed complement activation by interfering with anti-αGal antibody binding to cell surfaces, in particular donor organ endothelium. Accordingly, the pharmaceutical compositions of the invention may be administered alone, together with, or in seriatim with other therapy regimens for reducing the extent of binding of anti-αGal antibody to donor organ cells or tissue. In one embodiment, administration of the αGal oligosaccharide of the invention is combined with parenteral administration and/or extracorporeal treatment with column immobilized anti-agal idiotypic antibodies (for example, see U.S. Pat. No. 5,560,911). Other regimens that may accompany neutralization and/or depletion of anti-αGal antibodies using αGal oligosaccharides or pharmaceutically acceptable derivatives, include but are not limited to, extracorporeal treatment with column immobilized human anti-animal idiotypic antibodies (for example, see U.S. Pat. No. 5,560,911), plasmapheresis (in which all antibodies or specifically, one or more antibody types specific for antigenic epitopes on the surface of donor endothelial cells have been removed from the plasma) and perfusion of blood to be administered to the patient through organs, tissue or cells expressing αGal antigens (such as, for example, hearts, kidneys, erythrocytes, and cell lines derived from pig kidney, pig aortic endothelium, mouse endothelium, etc.).

Depletion of circulating anti-αGal antibody is a temporary solution, which can overcome the HAR crisis. But the antibody-producing B lymphocytes continue to produce antibody, which can pose a danger of longer-term antibody-mediated vascular rejection. These B lymphocytes bear on their membrane surface immunoglobulin with the αGal-binding domain exposed (Geller et al. 1993, Transplantation 55:168–172).

In particular embodiments, the administration of αGal oligosaccharides or pharmaceutically acceptable derivatives thereof targets cytocidal agents or complement-mediated lytic attack to B lymphocytes expressing anti-αGal idiotypes, thereby ablating the host's ability to mount the antibody response. This administration may be prior to, during, or subsequent to xenotransplantation and is directed toward reducing both the production and regeneration of anti-αGal antibodies. The dosage and frequency of administration is determined by the number of idiotype-bearing B lymphocytes present in peripheral blood, which may be quantified using techniques described in Section 5.4 or known in the art.

One embodiment encompasses the administration of an αGal oligosaccharide chemically linked to a cytocidal agent. Such cytocidal agents include, but are not limited to, toxins and cytotoxic drugs. Effective targeting of the αGal oligosaccharide/cytocidal agent complex to B lymphocytes bearing anti-αGal idiotypes requires avoidance of circulating anti-αGal antibodies to permit access to the B-cells. Accordingly, it is preferred that this complex is administered following ex vivo depletion of anti-αGal antibodies. Such depletion treatment may include, but is not limited to, extracorporeal exposure of host serum or plasma to αGal oligosaccharides, derivatives and/or anti-αGal idiotypic antibodies bound to a biologically inert matrix or a pig organ.

In another embodiment, αGal oligosaccharide compositions of the invention are used to target anti-αGal antibodies to the B-cells that produced them via drawing in a complement-mediated lytic attack. According to this embodiment, a complex comprising at least two αGal epitopes is administered to a patient, preferably following ex vivo treatment to deplete anti-αGal antibodies in the serum of the patient. While not wishing to be bound by theory, it is proposed that one of the αGal epitopes of this complex would be bound by the B-cell's surface immunoglobulin, while the remaining αGal epitope(s) would be displayed outward, serving as surface ligands for the circulating anti-αGal antibodies. In specific embodiments, the complex comprises at least 2, 3, 4, 5, 6, 7, 8, 9, 10, 15 or 20, αGal epitopes as a single molecule or multivalent. In preferred embodiments, the complex comprises 2 or 3 αGal epitopes. In another preferred embodiment, all but one, of the αGal epitopes of the complex are "masked" by a labile group as described in Section 5.1.1. While not wishing to be bound by theory, it is believed that by masking all but one αGal epitope of the complex, this treatment would minimize the risk of the formation of large circulating immune complexes, which could give rise to congestive events in the renal, glomerular, hepatic or pulmonary capillary networks, etc. According to this embodiment, the exposed αGal epitope binds the B-cell surface immunoglobulin and the masking group is gradually removed by natural or pharmacological intervention, exposing the previously masked αGal group, and bringing about complement-mediated lytic attack of the B-cells. Effective targeting of the αGal oligosaccharide/cytocidal agent complex to B lymphocytes bearing anti-αGal idiotypes requires avoidance of circulating anti-αGal antibodies to permit access to the B-cells. Accordingly, it is preferred that this complex is administered while the anti-αGal antibody titer has been reduced to negligible by treatments that include, but are not limited to: ex vivo depletion using a column bearing an αGal-oligosaccharide or anti-αGal idiotypic antibodies, or by using an organ from the donor species; in vivo infusion of soluble αGal oligosaccharide; absorption of anti-αGal antibodies by the xenograft; or a combination of these events.

In another embodiment, the ex vivo depletion of anti-αGal antibodies using αGal oligosaccharides or pharmaceutically acceptable derivatives of the invention is followed by the administration of anti-αGal idiotypic antibodies capable of binding to the surface of B lymphocytes and mediating the destruction of these cells either directly (e.g., where the antibodies are associated with or conjugated to a cytocidal agent), or through triggering complement-mediated lytic attack if conjugated to or associated with a cytocidal agent. Cytotoxic recombinant ScFvs may be generated using techniques known in the art. See, e.g., George, A. J. T., The Second Annual IBC International Conference on Antibody Engineering, San Diego, Calif., Dec. 16–18, 1991, incorporated herein by reference in its entirety.

The invention also encompasses the administration of αGal oligosaccharides of the invention to target anti-αGal antibody directed complement-mediated lytic attack to specific tissue and cell types. Thus, the invention provides for targeting complement-mediated lytic attack to a tissue, cell type, or organism expressing a distinguishing marker, by administering an effective amount of a αGal oligosaccharide or pharmaceutically acceptable derivative of the invention comprising a ligand for such marker. Examples of such arkers include, but are not limited to, tumor specific ntigens to which antibodies have been developed or may be routinely identified and generated using techniques known in the art.

In one embodiment, an αGal oligosaccharide composition of the invention comprising an autoantigenic peptide is administered to target anti-αGal antibodies to the MHC of autoreactive lymphocytes. In specific embodiments, the administered composition comprises one or more peptides selected from the group consisting of myelin basic protein peptides in Multiple Sclerosis, pancreatic islet autoantigenic peptides on p54 in juvenile (type I or autoimmune) diabetes mellitus, acetylcholine receptor peptides in myasthenia gravis and collagen peptides in rheumatoid arthritis).

In another embodiment, an αGal oligosaccharide composition of the invention comprising a ligand for a molecule required for lymphocyte activation is administered to target anti-αGal antibody mediated lytic attack to cells expressing this molecule. In a specific embodiment, the administered composition comprises an αGal oligosaccharide and the CD22 ligand NeuAcα2-6Galβ1-4GlcNAc. In another specific embodiment, the administered composition comprises a monoclonal antibody that binds CD22. Such monoclonal antibodies may be routinely generated using techniques known in the art or obtained commercially. This treatment is directed toward complement-mediated lytic attack of cells expressing the CD22 molecule required for B-T-cell cooperation during lymphocyte activation.

In another embodiment, an αGal oligosaccharide composition of the invention comprising a ligand bound by a pathogenic virus or by a virally infected cell is administered to target anti-αGal antibody-mediated lytic attack to the virus or infected cell. In specific embodiments, the administered composition comprises CD4-derived peptide bound by gp120 of HIV (from the D1 domain of CD4 and distinct from the MHC-binding region) and/or chemokine receptor derived peptide bound by gp120 of HIV (from the V3 domain of preferably fusin (Feng et al., 1996, Science 272:872–877) or the CC CKR-5 receptor (Samson et al., 1996, Biochemistry 35:3362–3367)). In another specific embodiment, the administered composition comprises NeuAcα2-6Galβ1-4Glc ligand for influenza virus, a recessed hemagglutinin ligand which is conserved among the main serotypes of the virus.

In another embodiment, an αGal oligosaccharide composition of the invention comprising a ligand bound by a parasite is administered to target anti-αGal antibody-mediated lytic attack to the parasite. In a specific embodiment, the administered composition comprises NeuAcα2-3Gal and thereby directs the complement-mediated lytic attack of cells expressing the trypanosoma trans-sialidase that binds NeuAcα2-3Gal.

Modifications of the invention in addition to those described above for treating cancer, autoimmunity disorders, immunosuppression, viral diseases and parasitic diseases will become apparent to those skilled in the art form the foregoing description. Additionally, upon reading the present disclosure, it will become apparent to those skilled in the art that the compositions of the invention may be administered to target anti-αGal antibody-mediated lytic attack to any therapeutically significant target for which a "homing molecule" (e.g., monoclonal antibody, receptor ligand etc.) has been or can be routinely identified, isolated and/or generated. Such modifications are intended to fall within the scope of the appended claims.

5.6. THERAPEUTIC COMPOSITIONS AND METHODS OF ADMINISTERING

The pharmaceutical compositions of the invention are useful in attenuating xenograft rejection and/or targeting anti-αGal directed complement-mediated lytic attack of targeted tissue and cell types. These compositions contain as an active ingredient, one or more distinct αGal oligosaccharides and/or pharmaceutically acceptable derivatives thereof. The αGal oligosaccharide composition of the invention can be administered to a patient either by itself, in combination with other pharmaceutical agents, and/or in pharmaceutical compositions where it is mixed with suitable carriers or excipient(s).

Pharmaceutical compositions suitable for use in the present invention include compositions wherein the active ingredients are contained in an effective amount to achieve its intended purpose. Effective dosages of the αGal compositions of the invention to be administered may be determined through procedures well known to those in the art which address such parameters as biological half-life, bioavailability, and toxicity. Such determination is well within the capability of those skilled in the art, especially in light of the detailed disclosure provided herein. For example, from the data presented in Section 6, it is determined that monovalent αGal pentasaccharide and αGal trisaccharide are efficacious in vivo at doses required to achieve circulating concentrations of 1 mM or greater. In addition to the active ingredients these pharmaceutical compositions may contain suitable pharmaceutically acceptable carriers comprising excipients and auxiliaries which facilitate processing of the active compounds into preparations which can be used pharmaceutically.

5.6.1. DOSAGE

According to the method of the invention, attenuation of the hyperacute rejection of a xenograft is achieved by the administration of a therapeutically effective amount of an αGal oligosaccharide and/or pharmaceutically acceptable derivative of the invention, i.e., a dose sufficient to bind to and/or neutralize anti-αGal antibodies in the serum of a patient. For example, monovalent αGal pentasaccharide or monovalent αGal trisaccharide may be administered as an infusions to attain steady state serum concentrations of 0.5–12 mM for 9–21 days, preferably for at least 14 days. Preferable blood concentrations of the monovalent αGal trisaccharide or αGal pentasaccharide are from 1–1.5 mM or 1.5–2.0 mM. A most pref erred dosage is about 1 mM.[1] Doses for multivalent αGal trisaccharide or αGal pentasaccharide are expected to be lower (in the μM αGal epitope range) and may be determined using techniques known in the art. Desirable blood levels may be maintained by a continuous infusion of the αGal oligosaccharide and/or pharmaceutically acceptable derivative comprising compositions of the invention as ascertained by plasma levels measured by techniques known in the art, such as HPLC (see e.g., Fu et al., U.S. application Ser. No. 08/563,822, filed Nov. 28, 1995, which is herein incorporated by reference in its entirety). Alternatively, doses of an αGal oligosaccharide and/or pharmaceutically acceptable derivative of the invention may be administered in intervals of from about once per day to 4 times per day. For example, a preferred dose is administered to achieve steady state serum concentrations of monovalent αGal trisaccharide, αGal pentasaccharide, or a pharmaceutically acceptable derivative thereof, of 1–1.5 mM or 1.5–2.0 mM. A most preferred dosage achieves a steady state serum concentration of about 1 mM. This may be achieved by the sterile injection of a 2.0% solution of the administered ingredients in buffered saline (any suitable saline solutions known to those skilled in the art of chemistry may be used).

[1] To achieve a steady state serum concentration for monovalent αGal pentasaccharide of 1 mM (i.e., 0.9 mg/mL) in a human patient of 70 Kg, it is estimated that a loading dose of 412 mg/Kg be administered in the form of a bolus or 15 minute infusion, followed by a continuous infusion of 30 g/h over a 14 day period (see Table 2 for further αGal trisaccharide and αGal pentasaccharide 2 infusion regimens).

When administering multivalent αGal oligosaccharides, it is preferred that dosage is carefully titrated upwardly and the serum is monitored to minimize immune complex formation.

Effective amounts of the therapeutic agents, e.g., classical immunosuppressive agents to be used in combination with the αGal oligosaccharide compositions of the invention are based on the recommended doses known to those skilled in the art for the such agents. For example, doses for cyclosporine would be directed toward maintaining a whole blood level of 200–300 mg/ml, as measured by HPLC; cyclophosphamide at the dosage of 0.5–2 mg/kg/day; and prednisone at 1 mg/kg/day in divided doses (Cooper, D. K. C., Immediate Postoperative Care and Maintenance Immunosuppressive Therapy, pp. 89–100 in Cooper, D. K. C. and Novitzky, D., eds., The Transplantation and Replacement of Thoracic Organs (Kluwer, Dordrecht 1990)). Minimization of possible side-effects can be found in standard physician reference texts. It should be noted that the attending physician would know how to and when to terminate, interrupt, or adjust therapy to lower dosage due to toxicity, bone marrow, liver or kidney dysfunctions or other adverse drug interaction. Conversely, the attending physician would also know to adjust treatment to higher levels if the clinical response is not adequate (precluding toxicity).

A therapeutically effective dose refers to that amount of the compound sufficient to result in amelioration of signs and symptoms associated with xenograft rejection, or a prolongation of xenograft survival in a patient. In applications where pharmaceutical compositions of the invention target anti-αGal antibody complement-mediated lytic attack of targeted tissues or cell types, a therapeutically effective dose refers to that amount of the compound sufficient to prevent activation of the complement pathway. Toxicity and therapeutic efficacy of such compounds can be etermined by standard pharmaceutical procedures in cell cultures or experimental animals that produce anti-αGal antibodies, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays using cells that express αGal antigenic determinants on their surface, such as, for example, porcine PK-15 pig kidney endothelial cells, pig aortic endothelial cells, and murine MAE cells. Preferably, these cells are from the same species as the donor and most preferably from the same tissue-type as the tissue to be transplanted. A dose may be formulated in animal models to achieve a circulating plasma concentration range that includes the $IC_{50}$ (i.e., the concentration of the test compound which achieves in a half-maximal neutralization and/or binding of anti-αGal antibodies in serum of a patient compared to a control that has not been treated with the αGal oligosaccharide compositions of the invention, as determined in cell culture. Such information can be used to more accurately determine useful doses in humans. For example, Table 2 in Section 6.6 provides estimated doses of monovalent αGal trisaccharide and αGal pentasaccharide required to obtain steady state serum concentrations of 0.5, 1.0 and 2.0 mM. Doses calculated in Table 2 were based on in vivo serum analysis of the pharmokinetic profile (See Table 1) and serum anti-αGal antibody neutralizing capacity in baboons of monovalent αGal trisaccharides and αGal pentasaccharides. Levels in plasma may be measured, for example, by high performance liquid chromatography (HPLC). See e.g., Fu et al., U.S. application Ser. No. 08/563,822, filed Nov. 28, 1995, which is herein incorporated by reference in its entirety. The exact formulation, route of administration and dosage can be chosen by the individual physician in view of the patient's condition. (See e.g., Fingl et al., 1975, in "The Pharmacological Basis of Therapeutics", Ch. 1 p1).

5.6.2. ROUTES OF ADMINISTRATION

Pharmaceutical compositions comprising αGal oligosaccharide or pharmaceutically acceptable derivative thereof can be administered to a patient, preferably a human or old world monkey, by itself, or in pharmaceutical compositions where it is mixed with suitable carriers or excipient(s) at doses to ameliorate symptoms associated with xenograft rejection, prolong xenograft survival in a patient or to direct complement-mediated lytic attack of targeted tissue or cell types.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for the form of administration desired.

The pharmaceutical compositions of the invention may be administered using techniques well known to those in the art. Preferably agents are formulated and administered systemically. Techniques for formulation and administration of the compounds of the invention may be found in "Remington's Pharmaceutical Sciences," 18th ed., 1990, Mack Publishing Co., Easton, Pa, latest edition. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. The preferred routes of administration are by intravenous infusion, intravenous injection, and intramuscular injection. Dosage forms include but are not limited to tablets, troches, dispersions, suspensions, suppositories, solutions, capsules, gels, syrups, slurries, creams, patches, minipumps and the like.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained in the form of a solid excipient, optionally by grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics.

Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

For clarity of discussion, the invention is described in the subsections below by way of example for the αGal pentasaccharide to neutralize anti-αGal antibodies and to attenuate xenograft rejection. However, the principles disclosed herein may be applied to other αGal oligosaccharides in attenuating xenograft rejection and in the use of compositions comprising αGal oligosaccharides to target complement-mediated lytic attack to specific cells containing a surface marker, such as, for example, anti-αGal antibody producing B-cells.

6. EXAMPLES

6.1. ENZYMATIC SYNTHESIS OF αGAL TRISACCHARIDE

N-acetylglucosamine (GlcNAc) was dissolved in 5 mM sodium phosphate buffer at 15 mM, and UDP-Gal, synthesized organically, using techniques known in the art, was then added to a final concentration of 5 mM. A bacterial lysate containing recombinant *Neisseria polysaccharea* β1,4-galactosyltransferase was then added to this mixture to a final activity of 10 μmoles/min/L. The DNA encoding this β1,4-galactosyltransferase was generated by the polymerase chain reaction (PCR) using techniques known in the art (see e.g., Innis, M., 1990, PCR protocols, a Guide to Methods and Applications, Academic Press, California; and Dieffenbach, W., 1995, PCR Primer, a Laboratory Manual, Cold Spring Harbor Press, New York). The PCR reaction used primers corresponding to sequences flanking the β1,4-galactosyltransferase of *Neisseria gonorrhoea* (see U.S. Pat. No. 5,545,553) and *Neisseria polysaccharea* template DNA that was isolated using standard methods known in the art (see e.g., Maniatis, T., 1982, Molecular Cloning, A Laboratory Manual, 2d ed., Cold Spring Harbor Laboratory, Cold Spring Harbor, N.Y.; Current Protocols in Molecular Biology). The PCR generated DNA was then cloned into the pGEX expression vector (Pharmacia) using methods known in the art (see e.g., Maniatis, T., 1982, Molecular Cloning, A Laboratory Manual, 2d ed., Cold Spring Harbor Laboratory, Cold Spring Harbor, N.Y.; Current Protocols in Molecular Biology). The protein expressed by this expression construct is a fusion protein in which glutathione-S-transferase is fused to the amino terminal end of the β1,4-galactosyltransferase. Lysates containing this fusion protein were prepared from *E. coli* host cells that were transformed with the expression construct and in which expression of the construct had been induced through the addition of isopropylthiogalactoside (IPTG).

After 24 h at ambient temperature the reaction mixture containing N-acetyl-lactosamine (LacNAc) and unreacted starting materials was filtered to remove proteins and purified by cation (Dowex 50) followed by anion (Dowex 1) exchange chromatography with water elution. The flow-through material containing LacNAc was pooled, concentrated and diafiltered by reverse osmosis (RO).

Concentrated aqueous LacNAc was dissolved in phosphate buffer to a final concentration of 5 mM, and UDP-Gal, synthesized organically, using techniques known in the art, was then added to a final concentration of 6 mM. A bacterial lysate containing recombinant mouse α1,3-galactosyltransferase was then added to this mixture to a final activity of 15 μmoles/min/L. The DNA encoding this α1,3-galactosyltransferase was generated by the reverse-transcription polymerase chain reaction (RT-PCR) using techniques known in the art (see e.g., Innis, M., 1990, PCR protocols, a Guide to Methods and Applications, Academic Press, California; and Dieffenbach, W., 1995, PCR Primer, a Laboratory Manual, Cold Spring Harbor Press, New York). The nucleic acid sequence encoding the mouse α1,3-galactosyltransferase gene has previously been reported (Larsen, et al., 1989 PNAS 86:8227–8231). Primers used in the RT-PCR reaction were designed so as to amplify a cDNA fragment corresponding to the mouse α1,3-galactosyltransferase gene, but which lacks nucleic acid sequences encoding the first 60 amino acids of the protein, i.e., nucleic acids encoding the amino terminal cytoplasmic tail and membrane spanning region of the enzyme. Template mRNA used in the RT-PCR reaction was isolated from mouse kidney using standard methods known in the art (see e.g., Maniatis, T., 1982, Molecular Cloning, A Laboratory Manual, 2d ed., Cold Spring Harbor Laboratory, Cold Spring Harbor, N.Y.; Current Protocols in Molecular Biology). The PCR generated cDNA was then cloned into the pGEX expression vector (Pharmacia) using methods known in the art (see e.g., Maniatis, T., 1982, Molecular Cloning, A Laboratory Manual, 2d ed., Cold Spring Harbor Laboratory, Cold Spring Harbor, N.Y.; Current Protocols in Molecular Biology). The protein expressed by this expression construct is a fusion protein in which glutathione-S-transferase is fused to the amino terminal end of the modified α1,3-galactosyltransferase encoded by the PCR generated cDNA. Lysates containing this fusion protein were prepared from *E. coli* host cells that were transformed with the expression construct and in which expression of the construct had been induced through the addition of IPTG.

After 24 h at 37° C., the reaction mixture, containing αGal-LacNAc and unreacted starting materials was filtered and purified by cation (Dowex 50) followed by anion (Dowex 1) exchange chromatography with water elution. The flow-through material was concentrated by RO. The concentrated α-Gal-LacNAc solution was mixed with acetonitrile (30:70), applied to a preparative amino-bonded silica HPLC column, and eluted isocratically. The fractions containing α-Gal-LacNac (αGal trisaccharide) were pooled, concentrated and lyophilized.

6.2. ENZYMATIC SYNTHESIS OF αGAL PENTASACCHARIDE

Lactose was dissolved in 5 mM sodium phosphate buffer at mM, and UDP-GlcNAc, obtained by fermentation, using techniques known in the art, was then added to a final concentration of 5 mM. A bacterial lysate containing recombinant *Neisseria polysaccharea* β1,3-N-acetylglucosaminyltransferase was then added to this mixture to a final activity of 10 μmoles/min/L. The DNA encoding this β1,3-N-acetylglucosaminyltransferase was generated by the polymerase chain reaction (PCR) using techniques known in the art, with primers corresponding to sequences flanking the β1,3—N-acetylglucosaminyltransferase of *Neisseria gonorrhoea* (see U.S. Pat. No. 5,545,553) and *Neisseria polysaccharea* template DNA that was isolated using standard methods known in the art. The PCR generated DNA was then cloned into the pGEX expression vector (Pharmacia) using methods known in the art. The protein expressed by this expression construct is a fusion protein in which glutathione-S-transferase is fused to the amino terminal end of the β1,3-N-acetylglucosaminyltransferase. Lysates containing this fusion protein were prepared from *E. coil* host cells that were transformed with the expression construct and in which expression of the construct had been induced through the addition of IPTG.

At 24 h, β-galactosidase was added to break down unreacted lactose. After 48 h at ambient temperature, the reaction mixture containing LNT-II, the product of the reaction, and unreacted starting materials was filtered to remove proteins and purified by cation (Dowex 50) followed by anion (Dowex 1) exchange chromatography with water elution. The flow-through material containing LNT-II was pooled, concentrated, and diafiltered by RO.

Concentrated aqueous LNT-II was dissolved in phosphate buffer to a final concentration of 5 mM. UDP-Gal, synthesized organically, using techniques known in the art, was added to a final concentration of 6 mM. Recombinant *Neisseria polysaccharea* β1,4-galactosyltransferase, generated as described in Section 6.1, was then added as bacterial lysate to a final activity of 10 μmoles/min/L. After 24 h at ambient temperature, the reaction mixture, containing LNnT and unreacted starting materials was filtered to remove proteins, and purified by cation (Dowex 50) followed by anion (Dowex 1) exchange chromatography with water elution. The flow-through material containing LNnT was concentrated by RO.

Concentrated aqueous LNnT was dissolved in phosphate buffer to a final concentration of 5 mM, and UDP-Gal, synthesized organically, using techniques known in the art, was then added to a final concentration of 6 mM. A bacterial lysate containing recombinant mouse α1,3-galactosyltransferase, generated as described in Section 6.1, was then added to this mixture to a final activity of 15 μmoles/min/L.

After 24 h at 37° C. the reaction mixture, containing αGal-LNnT and unreacted starting materials, was filtered to remove proteins, and purified by ion exchange chromatography with water elution. The flow-through material was concentrated by RO. The concentrated α-Gal-LNnT solution was mixed with acetonitrile (30:70), applied to a preparative amino-bonded silica HPLC column, and eluted isocratically. The fractions containing αGal-LNnT (αGal pentasaccharide) were pooled, concentrated and lyophilized.

6.3. IN VITRO LAMININ ELISA ANALYSIS

In vitro laminin ELISA evaluation of αGal oligosaccharides as neutralizers of anti-αGal antibodies. Mouse laminin is a basement membrane glycoprotein that expresses 50–70 oligosaccharides terminating in Galα1-3Gal, i.e., the αGal motif (Arumugham et al., 1986, Biochem. Biophys. Aeta 883:112). In this assay, immobilization of mouse laminin on microtiter plates serves as a capture ligand for anti-αGal antibodies. This example shows that the binding of anti-αGal antibodies is inhibited to different extent by αGal oligosaccharides of different lengths and glycosidic bond structure and that the non-αGal oligosaccharides tested do not inhibit antibody binding. The example provides a method by which to determine the ability of αGal oligosaccharides and pharmaceutically acceptable derivative of the invention to bind to anti-αGal antibodies and to thereby remove these antibodies from the serum, neutralize anti-αGal antibodies, and/or target anti-αGal directed complement-mediated lytic attack to specific tissue or cell types. The example also provides a method by which the effectiveness of the methods of the invention can be evaluated and dosages determined.

6.3.1. MATERIALS AND METHODS

Sera were mixed with serial dilutions of αGal oligosaccharides (αGal-CHO) at 37° C. for 1 hour, then added to mouse laminin-coated microtiter plates and incubated for 1 hour to allow binding. The microtiter plates were coated with 20 μg/mL mouse laminin in 50 mM $NaHCO_3$ buffer, pH 9.5 at 4° C. overnight, blocked with SuperBlock solution (Pierce) for 2 hours, and then washed 3 times with SuperBlock solution. After washing excess serum away, bound IgG and IgM was measured by adding goat anti-human IgG (or IgM) conjugated to alkaline phosphatase and incubating for 1 hour, washing, and adding substrate (pNPP).

6.3.2. RESULTS

Binding of anti-αGal antibodies is inhibited to different extent by αGal oligosaccharides of different lengths (FIG. 1A and FIG. 1B). Non-αGal oligosaccharides (e.g., sucrose (represented by open squares) and Galβ1-4Gal, lactose, and Galβ1-4GlcNAcβ1-3 Galβ1-4Glc (data not shown) do not inhibit antibody binding.

Generally, the αGal trisaccharide (Galα1-3Galβ1-4GlcNAc, represented by the open circle) is a slightly better inhibitor of IgG (FIG. 1A) and IgM (FIG. 1B) binding to laminin than αGal pentasaccharide(Galα1-3Galβ1-4GlcNAcβ1-3Galβ1-4Glc, represented by the open triangle), which is a slightly better inhibitor of both IgG and IgM binding to laminin than αGal disaccharide (Galα1-3Gal, represented by the open diamond).

6.4. IN VITRO IMMOBILIZED αGAL OLIGOSACCHARIDE ELISA ANALYSIS

In vitro immobilized αGal oligosaccharide ELISA analysis evaluation of anti-αGal antibody titer and of αGal oligosaccharides as neutralizers of anti-αGal antibodies. This example provides an assay that may be applied to determine the ability of αGal oligosaccharides and pharmaceutically acceptable derivative of the invention to bind to anti-αGal antibodies and to thereby remove these antibodies from the serum or plasma, neutralize anti-αGal antibodies, and/or target complement-mediated lytic attack to specific tissue or cell types. Such an ELISA is additionally useful in clinical monitoring of anti-αGal antibodies in blood of patients in advance of, and following xenotransplantation of organs from animals that express the αGal epitope.

6.4.1. MATERIALS AND METHODS

The derivative of the αGal pentasaccharide (αGal pentasaccharide glycinamide) was synthesized and immobilized on N-oxysuccinimide microtiter plates (Costar) (0.5 mg/ml αGal pentasaccharide glycinamide) in bicarbonate buffer, pH 9.0, overnight at 4° C.; the plate was blocked first for 1 hour with 1M ethanolamine in the same buffer and secondly with phosphate buffered saline, pH 7.4, containing 1% bovine serum albumin and 0.05% Tween 20 and 0.02% $NaN_3$ or PBNT. PBNT was used for all three subsequent plate washes and as a diluent for the antibodies. Serum from a baboon was added for 1 hour following pre-incubation with various oligosaccharides for 1 hour at 37° C., and subsequently washed three times. Bound antibodies were identified by the addition of a goat anti-human IgG and IgM-alkaline phosphatase and incubated at room temperature for 1 hour, followed by the addition of the substrate pNPP. The optical density at 405 nM was recorded.

6.4.2. RESULTS

Serum IgG and IgM binding to immobilized αGal pentasaccharide glycinamide was not inhibited by sucrose, and minimally by Galβ1-4Gal (FIG. 2A and 2B). All αGal oligosaccharides tested inhibited binding of IgG and IgM. IgG binding was inhibitable to a greater extent than IgM by most αGal oligosaccharides, and its binding was also more sensitive to differences in the structure of the αGal oligosaccharides tested.

6.5. IN VITRO CYTOTOXICITY ANALYSIS

In vitro cytotoxicity evaluation of αGal oligosaccharides as neutralizers of anti-αGal antibodies. This example shows that cytotoxicity is inhibited slightly better by αGal trisaccharide than by αGal pentasaccharide.

6.5.1. MATERIALS AND METHODS

Sera were incubated with serial dilutions of αGal oligosaccharides at 37° C. for 1 hour, then added to αGal-expressing monolayers (pig kidney cells, PK-15) in Terasaki plates for 1 hour at 37° C. Cytotoxicity was mediated by either endogenous complement, or the sera were de-complemented (heat inactivated for 30 minutes at 56° C.) and exogenous (rabbit) complement was added. After washing away excess serum, the viable dye mix "live-dead" (calcein AM/ethidium homodimer (Molecular Probes Inc., Eugene Oreg.)) was added and monolayers were scored for viability by fluorescence microscopy.

6.5.2. RESULTS

The cytotoxicity results observed in representative individual humans is presented in FIG. 3A and FIG. 3B. Generally, the αGal trisaccharide (Galα1-3Galβ1-4GlcNAc) is a slightly better inhibitor of cytotoxicity than αGal pentasaccharide (Galα1-3Galβ1-4GlcNAcβ1-3Galβ1-4Glc). Similar results were obtained using mouse endothelial cells (MAE) or primary pig aortic endothelial cell cultures (data not shown).

6.6. IN VIVO BLOOD SERUM ANALYSIS

Pharmokinetics of αGal trisaccharides and αGal pentasaccharides in baboons. This example presents a study of the pharmokinetic profile and serum anti-αGal antibody neutralizing capacity in baboons of αGal trisaccharides and αGal pentasaccharides and previews the compounds' suitability for use in the prevention of hyperacute rejection of porcine organs xenotransplanted into baboons. The study reveals that the pharmokinetics of the αGal trisaccharides and αGal pentasaccharides in baboons are similar and that a minimal serum concentration of 1 mM of the αGal trisaccharide or αGal pentasaccharide is required to inhibit hyperacute rejection resulting from anti-αGal antibody directed complement-mediated lytic attack.

6.6.1. MATERIALS AND METHODS

The pharmacokinetics of the αGal trisaccharide compositions and the αGal pentasaccharide compositions were determined by delivering to one baboon by 15 minute intravenous bolus, 0.5 mMol/Kg of one oligosaccharide and 48 hours later, delivering 0.5 mmol/Kg of the second oligosaccharide, and for a second baboon, delivering the oligosaccharides according to the same procedure, but in the reverse order.

Three Baboons were outfitted with indwelling venous and arterial catheters to the femoral vessels, and held in place with the aid of a jacket. Oligosaccharides were administered through the catheter in a 15 minute continuous infusion. Blood samples (as plasma) were collected for the determination of oligosaccharide concentration by HPLC and (as serum) for the determination of antibody titers by ELISA and cytotoxicity (using techniques described in Sections 6.3, 6.4 and 6.5), as well as for complement and blood chemistry, at predetermined time intervals and volumes.

6.6.2. RESULTS

The analysis of reactive anti-αGal antibody by ELISA (binding to mouse laminin, αGal albumin neoglycoconjugates and PK-cells) indicate that with enough added αGal antibody oligosaccharide, αGal antibody binding and cytotoxicity can be inhibited (See e.g., FIG. 4, which shows inhibition of anti-αGal antibody cytotoxicity of MAE cells at concentrations of 1.0–2.0 mM in one of the baboons tested. The volume of distribution governs the magnitude of the plasma concentration at time 0 after bolus drug administration. It is used to calculate a loading dose. During a continuous infusion, the drug's clearance governs the steady-state concentration for a given infusion rate. The clearance is used to calculate the infusion rate needed to maintain a desired drug concentration. The half-life describes how quickly concentrations diminish with time. Mathematical formulations known in the art were applied to estimate the pharmacokinetic parameters of the αGal trisaccharide and αGal pentasaccharide. The pharmacokinetic parameter data, presented in Table 1, indicates that the pharmacokinetics of the αGal trisaccharide and αGal pentasaccharide in baboons are similar. Compared to other drugs, the volumes of distribution of these oligosaccharides are low, less than the extravascular water volume (<400 mL/kg). The clearance is typical of compounds eliminated by GFR (glomerular filtration rate). The half-life of these drugs would be expected to be about 50% longer in humans due to a lower rate of clearance.

TABLE I

| Pharmacokinetic Parameter | Units | αGal-LNnT (1003, 1015) | αGal-LacNAc (1003, 1015) |
|---|---|---|---|
| Volume of Distribution | mL/kg | 199, 230 | 288, 362 |
| Clearance | mL/min/kg | 2.93, 3.97 | 4.18, 4.88 |
| Half-Life | min | 47.3, 40.2 | 46.8, 51.5 |

The pharmacokinetic data presented in Table 1 were used to predict concentrations of monovalent αGal trisaccharide and αGal pentasaccharide required to attain steady state serum concentrations of 0.5, 1.0 and 2.0 mM, respectively, by mathematical formulations known in the art. This data is presented in Table 2.

TABLE 2

Calculated αGal trisaccharide and αGal pentasaccharide administration to attain 0.5, 1.0, and 2.0 mM steady state serum concentrations

|  | αGal-trisaccharide | | | αGal pentasaccharide | | |
| --- | --- | --- | --- | --- | --- | --- |
| Desired steady-state serum concentration (mM) | 0.5 | 1.0 | 2.0 | 0.5 | 1.0 | 2.0 |
| Desired steady-state serum concentration (mg/mL) | 0.26 | .52 | 1.05 | 0.45 | 0.9 | 1.79 |
| LOADING DOSE (bolus or 15 min infusion); mg/Kg | 191 | 382 | 764 | 206 | 412 | 824 |
| g/20 Kg baboon | 3.82 | 7.64 | 15.28 | 4.12 | 8.24 | 16.48 |
| CONTINUOUS INFUSION mg/min/Kg | 2.57 | 5.14 | 10.28 | 3.56 | 7.12 | 14.24 |
| mg/h/Kg | 154.2 | 308.4 | 616.8 | 213.6 | 427.2 | 854.4 |
| g/h/20 Kg | 3.08 | 6.17 | 12.34 | 4.27 | 8.54 | 17.09 |
| g/24 h/20 Kg | 74.0 | 148 | 296.1 | 102.6 | 205.2 | 410.1 |
| Kg/14 days | 1.04 | 2.08 | 4.15 | 1.44 | 2.88 | 5.74 |

6.7. IN VIVO XENOTRANSPLANTATION

Primate model for testing and application of αGal oligosaccharides and dosages thereof. Due to the many similarities between human and baboon immune systems (Neubauer et al., 1981, J. Immunogenetics, 8:433–442; Garver et al., 1980, Cytogenetics & Cell Genetics, 27:238–245; Brodsky et al., 1982, Immunogenetics, 155:151–166; Hammer, C., in Hardy, M. A. (ed.), Xenograft 25, 115–123 (Elsevier, N.Y., 1989); Stark, J. H., et al., Transplantation, 30 52(6):1072–1078 (December 1991); Hammer, C., in Cooper, D. K. C., et al. (eds.), Xenotransplantation, 429–438 (Springer-Verlag 1991)), and because of the large size of baboons, these animals are convenient experimental model recipients of pig organs. These non-human primates also express anti-pig antibodies, and reject pig organs hyperacutely (Lexer et al., 1986, J. Heart Transplant, 4:411–418; Ye, Y., Cooper, D. K. C., in Cooper, D. K. C., et al. (eds.), Xenotransplantation, 389–393 (Springer-Verlag 1991); Cooper et al., 1991, J. Heart Transplant, 7:238–246, 1988; Platt et al., 1991, Transplantation, 52(2):214–220). A normal porcine heart was transplanted into the neck of a normal baboon. αGal pentasaccharide was infused (i.v.) to establish and maintain blood oligosaccharide levels predicted to inhibit HAR until infusate was exhausted (See Table 2). The ability of i.v. infused αGal pentasaccharide to block hyperacute rejection (HAR) of porcine heart xenografted to the neck of a baboon was determined and blood levels of αGal oligosaccharide, anti-αGal antibodies, and serum or plasma cytotoxicity toward pig kidney and mouse endothelial cells was monitored and correlated with the onset of HAR.

6.7.1. MATERIALS LAND METHODS
XENOGRAFT HEART TRANSPLANTATION

The heart was excised from the pig donor and transplanted in the neck of the baboon recipient using techniques essentially as described by Cooper et al., 1993, Transplantation, 56:769–777.

OLIGOSACCHARIDE ADMINISTRATION

The two xenotransplant baboons were outfitted with an indwelling catheter to the femoral vein to infuse compound and a catheter to the femoral artery for blood sampling. Following the transplant procedure, but just prior to providing circulatory access to the xenograft, the oligosaccharide was administered by i.v. pump through the catheter in a 15 min loading dose, followed by continuous 4 hour infusion to achieve 2.5 mM blood concentration (as determined by calculations presented in Table 2). Blood samples (as plasma) were collected for the determination of oligosaccharide concentration by HPLC and (as serum) for the determination of antibody titers by ELISA and cytotoxicity (using techniques described in Sections 6.3, 6.4 and 6.5 infra), as well as for complement and blood chemistry, at predetermined time intervals. Blood specimens collected for plasma were immediately centrifuged and the plasma withdrawn and stored frozen at −20° C. Blood specimens collected for serum were clotted at 4° C. overnight and the withdrawn serum frozen at −20° C. The αGal pentasaccharide was prepared according to the enzymatic methods set forth in example 6.2 and stored as a dry, white, solid powder. The oligosaccharide was dissolved in 250 mL sterile infusion grade saline to a concentration of 0.154 g/mL, or 177 mM. Induction anesthesia was with ketamine hydrochloride 5 mg/kg/body weight in and 0.5 mg/kg of xylazine iv. Intravenous fluid of approximately 20 ml/kg body weight was given during the course of the operative procedure through either a peripheral or central vein. Atropine 0.5 mg/kg was given iv. The larynx was sprayed with 2% lidocaine. Endotracheal intubation was carried out. The endotracheal tube was taped to the maxilla. The pig or baboon was ventilated with a Harvard positive pressure ventilator. Anesthesia was maintained with nitrous oxide 2 L/min and oxygen 1 L/min and 0.2%–1.2% halothane, at a respiratory rate of approximately 10 to 20 breaths per minute depending on the size of the animal. Tidal volume (approximately 20–24 ml/kg) was also adjusted to suit the size of the animal, and the ventilatory pressure was adjusted to approximately 15 to cm $H_2O$. Blood gases were checked, and ventilation adjusted as necessary. Arterial pressure was monitored in the recipient baboon by intermittent automatic cuff recordings.

The intra-arterial line in the femoral artery allowed continuous monitoring of arterial pressure, and access for determination of blood gases. A suitable antibiotic was administered i.v. to the recipient before any incision was made, and was then administered i.v. at 12 hourly intervals for 72 hours. Blood cultures were taken on the day following the operation to ensure that further antibiotic therapy was not indicated.

After αGal pentasaccharide infusion, when the xenograft's heartbeat became weak and irregular, external color became blotchy, and swelling of the atria was observed, the donor heart was removed under ketamine sedation after removing the skin sutures to expose the heart and placing ligatures around the common carotid artery and internal jugular vein above and below the sites of anastomosis. The ligatures were tied down, and the heart excised.

The heart was divided at midventricular level, and clot and blood washed out with saline. A thin section across the ventricles was taken and sent for histopathological examination to confirm the presence or otherwise of rejection.

6.7.2. RESULTS

The only significant alteration in blood chemistry that was recorded was an increase in creatinine phosphokinase, which is a natural consequence of surgery. Hematology results were unremarkable. The pig hearts of the two baboons resumed beating shortly after the baboon blood flow was channeled through the xenograft. One heart had to be electrically shocked to initiate regular beating. Once the heartbeat resumed, regular color returned to the heart and an even beat was maintained for the duration of the four hour oligosaccharide infusion. At the end of infusion, heart beat became weak and irregular, external color became blotchy, and swelling of the atria was observed. At this time, more than 1 hour following cessation of the 4 hour αGal pentasaccharide infusion, the xenograft was excised. Hearts from normal pigs xenotransplanted into baboons in this fashion in the past, but without interference with immune functions, have been hyperacutely rejected without exception in 5–10 minutes. Analysis of reactive anti-αGal antibody by ELISA (binding to mouse laminin, α-Gal-albumin neoglycoconjugates and PK-15 cells) indicated pronounced reduction in the anti-αGal antibody titer coinciding with the period during which serum concentration of αGal oligosaccharide exceeded 1 mM (Data not shown).

Cytotoxicity of the baboon sera against MAE cells was reduced by 100% and against PK-15 by 85–95% during the 4 hours of αGal-LNnT infusion (FIGS. 5A and 5B). HPLC analysis of plasma samples revealed higher than expected blood levels of oligosaccharide in both xenotransplanted baboons. Blood concentrations increased steadily following release of blood flow through the pig heart reaching a plateau of 12 mM in the first baboon (FIG. 5A) and 5 mM in the second (FIG. 5B). These blood concentrations were approximately twice what was predicted by the earlier pharmacokinetic infusions in the same baboons in the absence of xenografting or anesthesia. It is probable that increased blood flow through the xenograft, which acts as an arterial-venous shunt, as well as the peripheral vasodilatation caused by the anesthetic isoflurene, resulted in a reduction in renal filtration rate. This effect would result in the reduced clearance rate of the infused oligosaccharide, and give rise to the observed accumulation of oligosaccharide in the baboons' circulation.

Essentially normal histology was observed during the initial 3 hours of infusion (data not shown). Only when the xenografts exhibited external deterioration was there evidence of vascular congestion, vascular and intersticial neutrophilia, and, in one baboon, fibrin deposition at the luminal surface of the endothelium. Immunofluorescence indicated IgG, IgM and complement (C3) deposition at the endothelial surface as early as 1.5 hours in the first baboon and not until 3 hours in the second baboon.

6.8. EXTRACORPOREAL DEPLETION OF ANTI-αGAL ANTIBODIES

Ex vivo depletion of anti-αGal antibodies from human serum by passage over αGal sepharose. This example shows that most of the cytotoxic antibody population in human serum can be absorbed upon perfusion through columns of a matrix containing αGal trisaccharide or αGal pentasaccharide.

6.8.1. MATERIALS AND METHODS

Pooled human serum was diluted 1:1 with phosphate buffered saline and passed over minicolumns (0.3 mL bed) containing beads to which αGal LacNAc (αGal trisaccharide), αGal-LNnT (αGal pentasaccharide) or glucose was coupled. Coupling of the αGal oligosaccharide compositions to the sepharose matrix was accomplished by reacting glycine amides of the carbohydrates with sepharose-bearing N-hydroxysuccinimide groups (Sigma) at pH 9.7 in sodium borate buffer, overnight at 4° C. Sepharose beads bearing glucose were purchased from Sigma.

Fractions were tested for cytotoxicity against pig PK-15 cells by live/dead assays as described in Sections 6.3, 6.4 and 6.5.

6.8.2. RESULTS

The cytotoxicity data observed for two different lots of serum passaged over beads bearing immobilized αGal-LacNAc and αGal-LNnT, is presented in FIG. 6A and FIG. 6B. The early fractions from the αGal oligosaccharide-immobilized beads exhibited greatly diminished cytotoxicity, indicating that the anti-αGal cytotoxic antibodies had been absorbed onto the αGal derivatized beads. The beads covered with αGal trisaccharide (αGal-LacNAc) removed most but not all of the cytotoxic activity from the first 50 mL serum, whereas the beads derivatized with αGal pentasaccharide (αGal-LNnT) removed nearly all of the cytotoxicity in the early fractions, and continued to remove cytotoxic antibodies for longer than the αGal trisaccharide derivatized beads. As demonstrated in FIG. 6B, beads derivatized with glucose were comparatively inefficient in removing cytotoxic antibodies.

The present invention is not to be limited in scope by the specific embodiments described herein, which are intended as single illustrations of individual aspects of the invention and functionally equivalent methods and components are within the scope of the invention. Indeed, various modifications of the invention, in addition to those shown and described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method for suppressing B-lymphocytes expressing anti-αGal idiotypes in a subject, comprising administering an amount of a composition comprising an αGal oligosaccharide linked to a cytocidal agent effective in binding anti-αGal idiotypes expressed on the surface of B-lymphocytes.

2. The method of claim 1, further comprising the step of contacting serum of the subject with an immobilized αGal oligosaccharide ex vivo.

3. The method of claim 1, wherein the cytocidal agent is selected from the group consisting of ricin A, *Pseudomonas exotoxin*, cytosine arabinoside and daunorubicin.

4. A method for treatment of a parasitic disease in a subject comprising administering an amount of a composition comprising an αGal oligosaccharide linked to a ligand that binds to a target located on a parasite.

5. The method of claim 4, wherein the target is selected from the group consisting of NeuAcα2-3Gal, trans-sialidase and a Gal/GalNAc-terminating oligosaccharide.

6. The method of claim 4, wherein the parasite is selected from the group consisting of *Trypanosoma cruzi, Plasmodium falciparum* and *Entamoeba histolytica*.

7. The method of claim 4, wherein the parasitic disease is selected from the group consisting of Chagas disease, malaria and amoebic dysentery.

8. The method of claim 1 or 4, wherein the αGal oligosaccharide is selected from the group consisting of Galα1-3Gal, Galα1-3Galβ1-4Glc, Galα1-3Galβ1-4GlcNAc, Galα1-3Galβ1-4GlcNAcβ1-3Gal and Galα1-3Galβ1-4GalNAcβ1-3Galβ1-4Glc.

* * * * *